(12) United States Patent
Ikezawa

(10) Patent No.: US 7,458,686 B2
(45) Date of Patent: Dec. 2, 2008

(54) OPTOMETRY APPARATUS

(75) Inventor: Yukio Ikezawa, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 340 days.

(21) Appl. No.: 11/135,349

(22) Filed: May 24, 2005

(65) Prior Publication Data

US 2005/0264760 A1    Dec. 1, 2005

(30) Foreign Application Priority Data

May 31, 2004    (JP)    ............................. 2004-162290

(51) Int. Cl.
*A61B 3/02*    (2006.01)
(52) U.S. Cl. ...................... 351/222; 351/223
(58) Field of Classification Search ................. 351/222, 351/223, 232, 237, 239, 241, 243
See application file for complete search history.

(56) References Cited

U.S. PATENT DOCUMENTS

| | | | | |
|---|---|---|---|---|
| 5,825,460 | A * | 10/1998 | Kohayakawa | ............... 351/237 |
| 6,045,227 | A * | 4/2000 | Stewart et al. | ............... 351/237 |
| 2004/0105073 | A1* | 6/2004 | Maddalena et al. | ......... 351/205 |

FOREIGN PATENT DOCUMENTS

| | | |
|---|---|---|
| JP | 7-43651 | 2/1995 |
| JP | 2002-119471 | 4/2002 |
| JP | 2002-119476 | 4/2002 |

OTHER PUBLICATIONS

Ophthalmologic Examination Method Handbook (Third Edition), Maruo, Koguchi, et al. al, Igaku-Shoin, 1999, pp. 11 and 12.

* cited by examiner

*Primary Examiner*—Joseph Martinez
(74) *Attorney, Agent, or Firm*—Edwards Angell Palmer & Dodge LLP

(57) ABSTRACT

Provided is an optometry apparatus capable of checking details of input operation performed by a person to be examined to smoothly perform an examination. The optometry apparatus includes: an optical head portion having a liquid crystal display device for indicating an index such as a Landolt ring to the left eye of the person to be examined; an optical head portion having a liquid crystal display device for indicating an index to the right eye of the person to be examined; a joystick lever for inputting a reply to the indices indicated by the liquid crystal display devices, which is operated by the person to be examined; and a control portion that causes the liquid crystal display devices to display operational detail information indicating operational details of the joystick lever operated by the person to be examined in addition to the indices.

28 Claims, 26 Drawing Sheets

FIG.17(A)
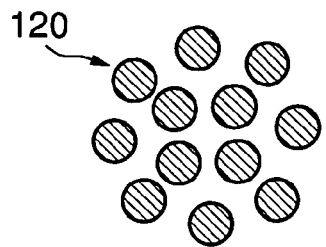 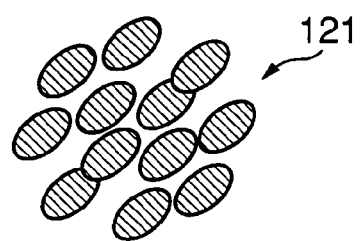
FIG.17(B)
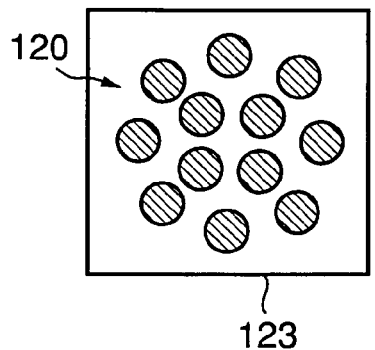 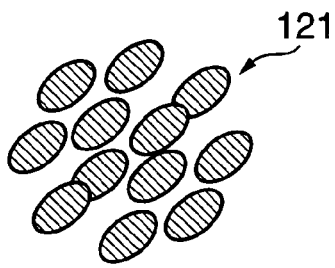
FIG.18(A)
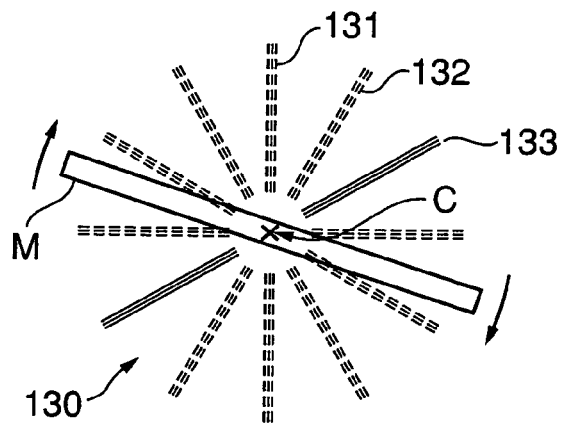
FIG.18(B)
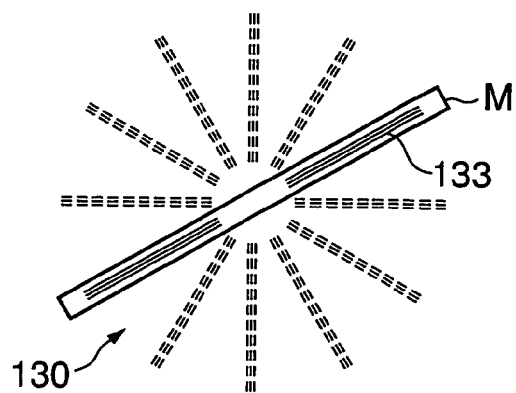

FIG.28(A)
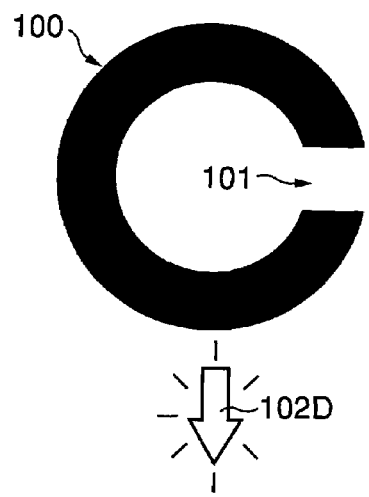
FIG.28(B)
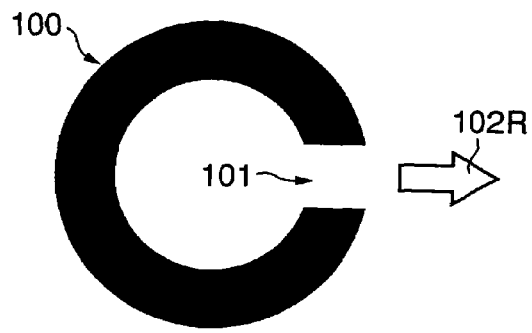
FIG.29(A)
Trial Input Operation of Eyesight Examination
Please Tilt the Lever in Direction
Corresoinding to Gap
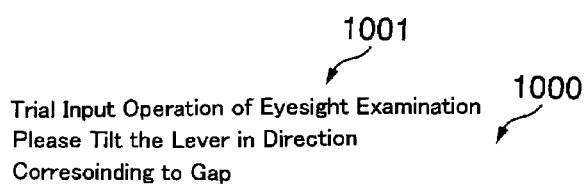
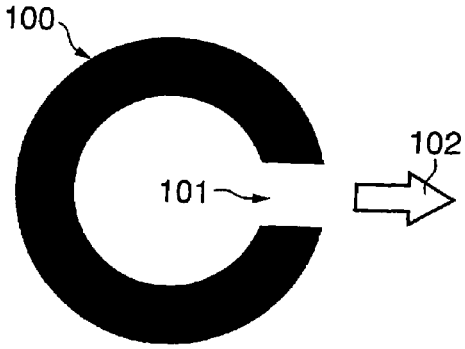
FIG.29(B)
Corret
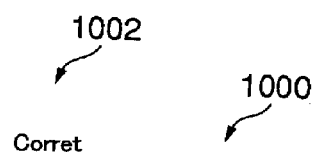
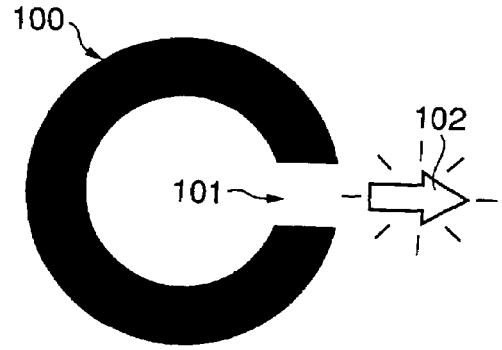

OPTOMETRY APPARATUS

BACKGROUND OF THE INVENTION

1. Field of the Invention

The present invention relates to an optometry apparatus for performing a subjective examination including: indicating various indices to a person to be examined; and obtaining an eyesight value of an eye to be examined based on appearance states of the indices.

2. Description of the Related Art

Up to now, subjective examinations have been widely performed in ophthalmologic fields, spectacle stores, and the like. In the subjective examinations, indices such as Landolt rings for eyesight measurement and fan charts for astigmatic measurement are indicated to a person to be examined and an eyesight value of an eye to be examined is obtained based on appearance states of the indices. In conventional subjective examinations, an examiner asks the person to be examined question about the appearance states of the indices. The examiner performs the selection of a next index to be indicated and the determination of the eyesight value based on the reply of the person to be examined.

In recent years, there has been proposed an optometry apparatus capable of performing both an objective examination for optically measuring the spherical power and cylindrical power of the eye to be examined and the above-mentioned subjective examination and attention has been given thereto. A structural example of such an optometry apparatus is disclosed in JP 2002-119476 A (claim 6, specification paragraphs [0039] to [0043]). The optometry apparatus includes an automatic alignment mechanism for automatically aligning an optometry unit with the eye to be examined, a manual alignment mechanism for manually aligning the optometry unit with the eye to be examined by a person to be examined, a determination unit for determining whether or not automatic alignment can be performed, and an informing unit for giving an explanation about the automatic alignment to the person to be examined to understand it.

An optometry system is disclosed in JP 2002-119471 A (claims 1 and 2, specification paragraphs [0023], [0038] to [0040], [0042] to [0044], and [0055] to [0058], and FIGS. 4 to 7). The optometry system includes a monitor for displaying an optometry measurement procedure such that a customer can perform optometry measurement. One of a moving image and a still image that indicate the measurement procedure is repeatedly displayed on the monitor until measurement data is obtained.

Each of the optometry apparatuses described in those documents has a function for guiding the person to be examined using a character message or a voice message. Therefore, there is a feature that the person to be examined can (substantially) independently perform examination sequences. The person to be examined operates an input device such as a joystick lever or a cursor key based on the guide to input reply information related to the appearance state of the index to the optometry apparatus. The optometry apparatus performs the selection of a next index to be indicated and the determination of an eyesight value based on the inputted information to automatically advance the subjective examination.

In such an optometry apparatus, when the indicated eyesight chart is switched to another chart, the person to be examined recognizes the measurement is shifted to a next stage. When a beep sound to be outputted in the case where an operational input to the joystick lever is enabled is generated, the person to be examined recognizes the receipt of the reply.

That is, according to such an optometry apparatus, the person to be examined can check the completion of the input operation but cannot check the details of the input operation. For example, assume that the person to be examined recognizes a correct answer "left" about a Landolt ring which is a circle with a left side gap in an eyesight examination using an eyesight chart including Landolt rings and then intends to tilt the joystick lever in a direction corresponding to the "left". However, when the person to be examined has tilted the joystick lever in a direction corresponding to, for example, an "upper left" by faulty operation, the optometry apparatus determines a "wrong answer" even in the case where the person to be examined has eyesight to check the Landolt ring. When the faulty operation occurs by such an input device, operation for obtaining a correct eyesight value of the eye to be examined requires a redundant time such as a reexamination time. Therefore, an examination time becomes unnecessarily long, with the result that a burden on the person to be examined increases.

Note that only the person to be examined can recognize the faulty operation, so it may be fundamentally impossible that the optometry apparatus actively determines whether or not the faulty operation is performed. Therefore, checking whether or not the faulty operation is performed depends on the recognition of the person to be examined. However, the conventional optometry apparatus cannot cause the person to be examined to check whether or not the faulty operation is performed.

In recent years, Early Treatment Diabetic Retinopathy Study (ETDRS) has improved the diffusion of indices of, a type in which eyesight is indicated based on the logarithm of a visual angle, that is, a log MAR (logarithm of minimum angle of resolution) type. In an eyesight chart of the log MAR type, indices having different sizes at a predetermined rate ($^{10}\sqrt{10}$) in each of stages of eyesight values are arranged at regular intervals (For example, see "Ophthalmologic Examination Method Handbook (Third Edition)", Maruo, Koguchi, et al, Igaku-Shoin, 1999, pp. 11 and 12.).

When the eyesight chart of the log MAR type is applied to an optometry apparatus that can perform an examination without depending on an examiner, it is difficult that the person to be examined recognizes a selected index. Therefore, a burden on the person to be examined is large. In addition, examination accuracy is likely to reduce. Those problems occur even in the case of using an eyesight chart for simultaneously indicating a plurality of indices to a person to be examined and then performing an examination while each of the indices is selectively provided to the person to be examined, such as an eyesight chart including a plurality of Landolt rings.

The optometry system disclosed in JP 2002-119471 A includes an optometry apparatus that can perform an examination with depending on the single person to be examined. In order to smoothly perform the examination, training screens for training an input device operating method and an examination procedure are displayed. The training screens are displayed on a monitor device connected with the optometry apparatus through a communication cable. The person to be examined must train while views the training screen on the monitor device provided separately from the optometry apparatus, so that training operation is complicated. When there is no location space, it is hard to locate the monitor device because it is separately provided. In addition, a structure in which the training screens are displayed on a monitor device of a computer terminal for examiner to perform training of input operation is expected. However, when the training operation is to be performed, the assistance of the examiner is required. This becomes a factor of inhibiting automation of an examination process.

SUMMARY OF THE INVENTION

The present invention has been made in view of the above-mentioned circumstances. An object of the present invention is to provide an optometry apparatus capable of checking the details of input operation performed by a person to be examined to smoothly perform an examination.

In addition, another object of the present invention is to provide an optometry apparatus capable of indicating an index selected by a person to be examined to the person to be examined in the case of using an eyesight chart of a type for simultaneously showing a plurality of indices, thereby reducing a burden on the person to be examined and improving examination accuracy.

Another object of the present invention is to provide an optometry apparatus in which training of input operation can be easily performed.

To achieve the above object, according to a first aspect of the present invention, there is provided an optometry apparatus, including: index indicating means for indicating an index to each of right and left eyes of a person to be examined; operation means for inputting a reply to the index, which is operated by the person to be examined, the reply to the index being performed by specifying a direction by the operation means; and display means for displaying the index and operational detail information expressing the direction specified by the operation means to the person to be examined.

According to a second aspect of the present invention, there is provided an optometry apparatus, including: index indicating means for indicating an index to each of right and left eyes of a person to be examined; operation means for inputting a reply to the index, which is operated by the person to be examined, the index being composed of a plurality of parts, the reply to the index being performed by selecting any one of the plurality of parts by the operation means; and display means for displaying the index and operational detail information expressing the part of the index selected by the operation means to the person to be examined.

According to a third aspect of the present invention, there is provided an optometry apparatus, including: index indicating means for indicating an index to each of right and left eyes of a person to be examined; operation means for inputting a reply to the index, which is operated by the person to be examined, the reply to the index being performed by specifying a position on the index by the operation means; and display means for displaying the index and operational detail information expressing the position specified by the operation means to the person to be examined.

According to a fourth aspect of the present invention, in an optometry apparatus according to the third aspect of the present invention, the index is a fan chart used for astigmatic examination, the display means displays a mark rotating about a central position of the fan chart to the person to be examined, and the reply is performed by operating the operation means to stop the mark which is rotating at a position corresponding to a visually dense portion on the fan chart.

According to a fifth aspect of the present invention, in an optometry apparatus according to the fourth aspect of the present invention, the optometry apparatus further includes means for obtaining an astigmatic axial angle corresponding to the position on the fan chart when the mark stops rotating.

According to a sixth aspect of the present invention, in an optometry apparatus according to the third aspect of the present invention, the index is a cross chart used for phoria examination, and the optometry apparatus further includes calculation means for calculating prism power corresponding to a predetermined position of the cross chart when the predetermined position is specified by the operation means.

According to a seventh aspect of the present invention, in an optometry apparatus according to any one of the first to third aspects of the present invention, the index indicating means is an eyesight chart including a first index to which a polarizing characteristic in a predetermined direction is provided and a second index to which a polarizing characteristic in a direction perpendicular to the predetermined direction is provided, and the optometry apparatus further includes polarization means for providing the polarizing characteristic in the predetermined direction to the left eye to be examined to make visual recognition of the first index and providing the polarizing characteristic in the direction perpendicular to the predetermined direction to the right eye to be examined to make visual recognition of the second index.

According to an eighth aspect of the present invention, there is provided an optometry apparatus, including: index indicating means for indicating an eyesight chart including a plurality of indices to each of right and left eyes of a person to be examined; operation means for inputting a reply to an index included in the indicated eyesight chart, which is operated by the person to be examined, the operating means being operated to select and specify the index included in the indicated eyesight chart; and display means for displaying the indicated index and operational detail information expressing the index specified by the operation means to the person to be examined.

According to a ninth aspect of the present invention, in an optometry apparatus according to any one of the first to eighth aspects of the present invention, the display means blinks the operational detail information for a predetermined time and the optometry apparatus further includes: reentry request operation means for requesting reentry of the reply to the index for the predetermined time; and control means for setting the blinked operational detail information into a non-display state and enabling the reentry of the reply to the index when the reentry request operation means is operated.

According to a tenth aspect of the present invention, in an optometry apparatus according to any one of the first to eighth aspects of the present invention, the optometry apparatus further includes: reentry request operation means for requesting reentry of the reply to the index for the predetermined time, which is operated by the person to be examined; and control means for setting the displayed operational detail information into a non-display state and enabling the reentry of the reply to the index when the reentry request operation means is operated.

According to an eleventh aspect of the present invention, in an optometry apparatus according to any one of the first to eighth aspects of the present invention, the optometry apparatus further includes training screen displaying means for displaying a training screen for training an operating method of the operation means for various examinations to the person to be examined, and when input operation executed by the operation means on the training screen is fit to the operating method, the display means displays correct information indicating that the input operation is correct as the operational detail information and when the input operation is not fit to the operating method, the display means displays incorrect information indicating that the input operation is incorrect as the operational detail information.

According to a twelfth aspect of the present invention, in an optometry apparatus according to any one of the first to eleventh aspects of the present invention, the index indicating means and the display means are each composed of a single liquid crystal display device.

According to a thirteenth aspect of the present invention, in an optometry apparatus according to any one of the first to eleventh aspects of the present invention, the display means includes a plurality of light emitting devices arranged around the index indicated by the index indicating means and the display means displays the operational detail information by turning on a light emitting device located at a position corresponding to operation of the operation means.

According to the optometry apparatus of the present invention, the operational detail information indicating the operational detail of the operation means operated by the person to be examined, which is a reply to the index, is displayed to the person to be examined in addition to the index. Therefore, when the person to be examined compares the intended replay with the operational detail indicated by the operational detail information, the person can check whether or not the faulty operation of the operation means occurs. Thus, a situation in which the examination proceeds while a problem related to the faulty operation is left can be prevented from occurring, so it is possible to smoothly perform the examination.

According to the eighth aspect of the present invention in the optometry apparatus, the operational detail information indicating the index specified by the person to be examined out of the plurality of indices included in the eyesight chart is displayed to the person to be examined in addition to the index. Therefore, the person to be examined can clearly recognize the index specified thereby. Thus, a burden on the person to be examined during the examination using the eyesight chart is reduced. In addition, there is no erroneous reply to an index different from the specified index, so the examination accuracy is improved.

According to the eleventh aspect of the present invention in the optometry apparatus, "correct information" or "incorrect information" is displayed to the person to be examined according to whether or not the input operation is suitably performed at the time of training the operating method of the operation means. Therefore, the person to be examined can easily check whether or not the input operation is suitable. Thus, it is possible to easily perform the training of the operating method of the operation means.

BRIEF DESCRIPTION OF THE DRAWINGS

In the accompanying drawings:

FIGS. 9A to 9C are schematic views each showing an example of the structure of the measurement optical system included in the optometry apparatus according to the first embodiment of the present invention, in which FIG. 9A is a schematic structural view showing an index indicated to a left eye of a person to be examined, FIG. 9B is a schematic structural view showing an index indicated to a right eye thereof, and FIG. 9C is a schematic view showing a visual state in which right and left indices are fused with each other;

FIGS. 15A and 15B are schematic views each showing an example of a display pattern of an image displayed to the person to be examined by the optometry apparatus according to the first embodiment of the present invention, in which FIG. 15A shows a pattern of an eyesight chart (Landolt ring) indicated to the person to be examined for eyesight measurement and FIG. 15B shows a display pattern of operational detail information based on a reply of the person to be examined to the eyesight chart;

FIGS. 17A and 17B are schematic views showing an example of a display pattern of an image displayed to the person to be examined by the optometry apparatus according to the first embodiment of the present invention and an example of a visual state of the person to be examined, visually recognizing the image, in which FIG. 17A shows a display pattern of a pair of right and left dot charts indicated to the person to be examined for astigmatic measurement and the visual state of the person to be examined and FIG. 17B shows a display pattern of operational detail information based on a reply of the person to be examined to the dot charts;

FIGS. 18A and 18B are schematic views showing an example of a display pattern of an image displayed to the person to be examined by the optometry apparatus according to the first embodiment of the present invention and an example of a visual state of the person to be examined, visually recognizing the image, in which FIG. 18A shows a display pattern of a fan chart indicated to the person to be examined for astigmatic measurement and the visual state of the person to be examined and FIG. 18B shows a display pattern of operational detail information based on a reply of the person to be examined to the fan chart;

FIGS. 19A to 19C are schematic views each showing an example of a display pattern of an image displayed to the person to be examined by the optometry apparatus according to the first embodiment of the present invention, in which FIG. 19A shows a pattern of a red-green chart indicated to a right eye of the person to be examined to perform a red-green test for measuring spherical power of the eye to be examined with high precision, FIG. 19B shows a pattern of a red-green chart indicated to a left eye of the person to be examined, and FIG. 19C shows a display pattern indicating a state in which the red-green charts for right and left eyes are fused and a display pattern of operational detail information based on a reply of the person to be examined;

FIGS. 20A and 20B are schematic views each showing an example of a display pattern of an image displayed to the person to be examined by the optometry apparatus according to the first embodiment of the present invention, in which FIG. 20A shows an example of a visual state of the person to be examined, visually recognizing a cross chart indicated for phoria examination and FIG. 20B shows a display pattern of operational detail information based on a reply of the person to be examined to the cross chart;

FIGS. 21A and 21B are schematic views showing an example of a display pattern of an image displayed to the person to be examined by the optometry apparatus according to the first embodiment of the present invention and an example of a visual state of the person to be examined, visually recognizing the image, in which FIG. 21A shows a display pattern of a near chart indicated to the person to be examined for near examination and the visual state of the person to be examined and FIG. 21B shows a display pattern of operational detail information based on a reply of the person to be examined to the near chart;

FIGS. 28A and 28B are schematic views each showing an example of a display pattern of an image displayed to the person to be examined by the optometry apparatus according to the third embodiment of the present invention, in which FIG. 28A shows a state in which operational detail information based on a reply of the person to be examined to a Landolt ring is blinked and FIG. 28 shows a display state of the operational detail information when the reply of the person to be examined is inputted again;

FIGS. 29A and 29B are schematic views each showing an example of a display pattern of an image displayed to the person to be-examined by an optometry apparatus according to a fourth embodiment of the present invention, in which FIG. 29A shows a pattern of an eyesight examination training screen using a Landolt ring and FIG. 29B shows a pattern of a screen displayed when the person to be examined performs correct operation on the training screen;

FIGS. 30A and 30B are schematic views each showing an example of a structure of a measurement optical system included in the optometry apparatus according to the first embodiment of the present invention, in which FIG. 30A is a side view showing a structure of a part of the measurement optical system and FIG. 30B is a front view showing the structure of the part of the measurement optical system.

DETAILED DESCRIPTION OF THE PREFERRED EMBODIMENTS

Examples of an optometry apparatus according to embodiments of the present invention will be described in detail with reference to the accompanying drawings.

First Embodiment

Figure 1:
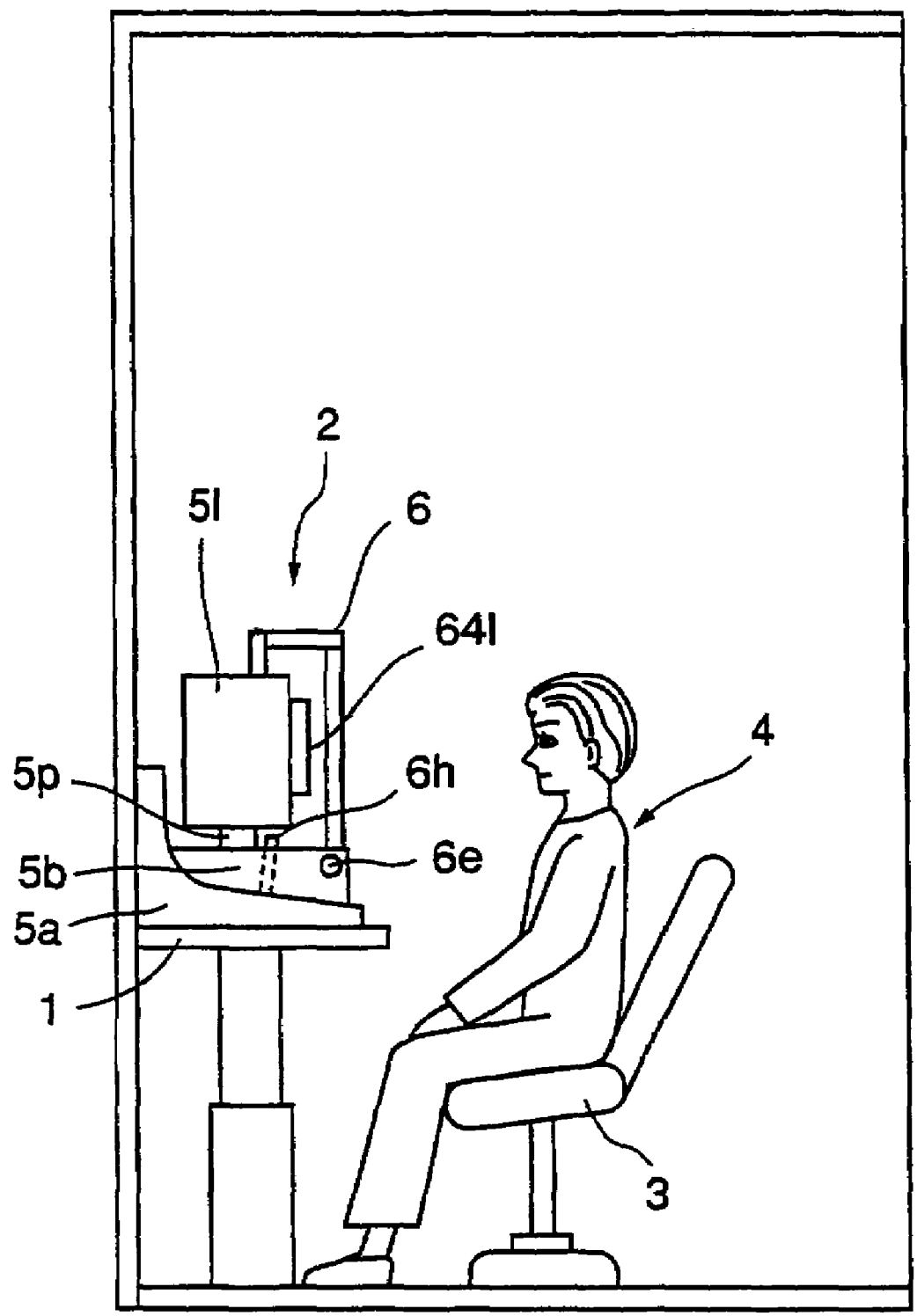
FIG. 1 is a schematic side view showing an example of an external structure of an optometry apparatus according to a first embodiment of the present invention.
Figure 2:
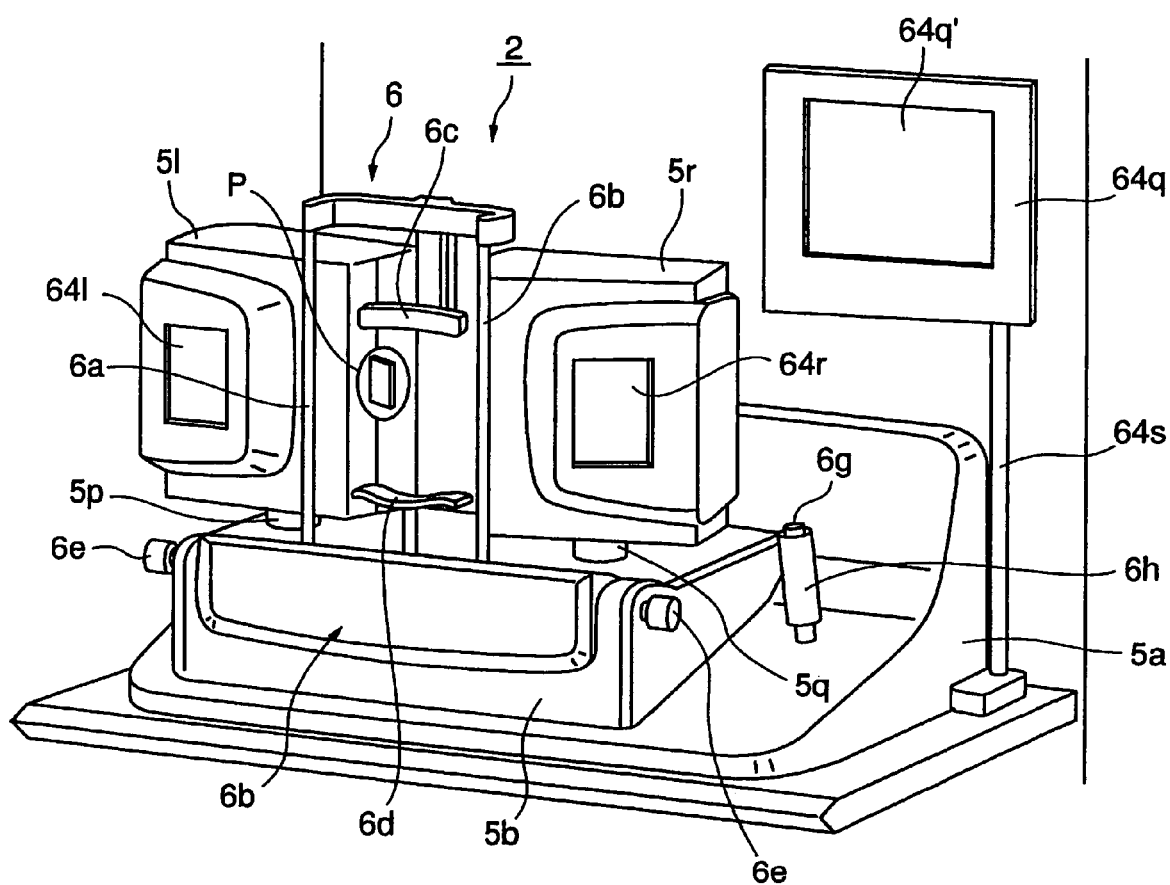
FIG. 2 is a schematic perspective view showing an example of the external structure of the optometry apparatus according to the first embodiment of the present invention.
Figure 11:
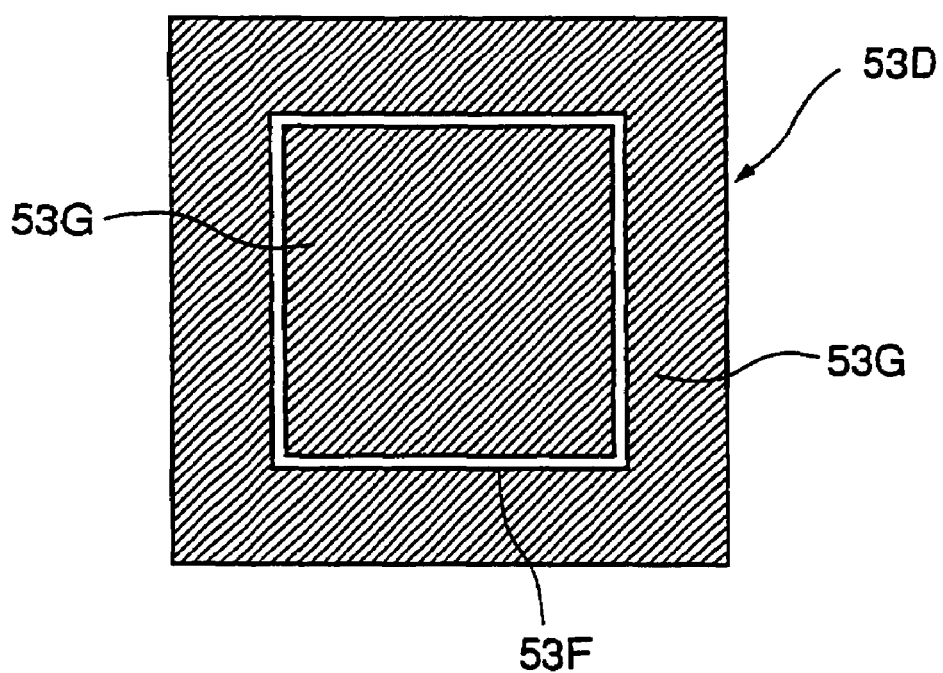
FIG. 11 is a schematic view showing an example of the structure of the measurement optical system included in the optometry apparatus according to the first embodiment of the present invention.
Figure 12:
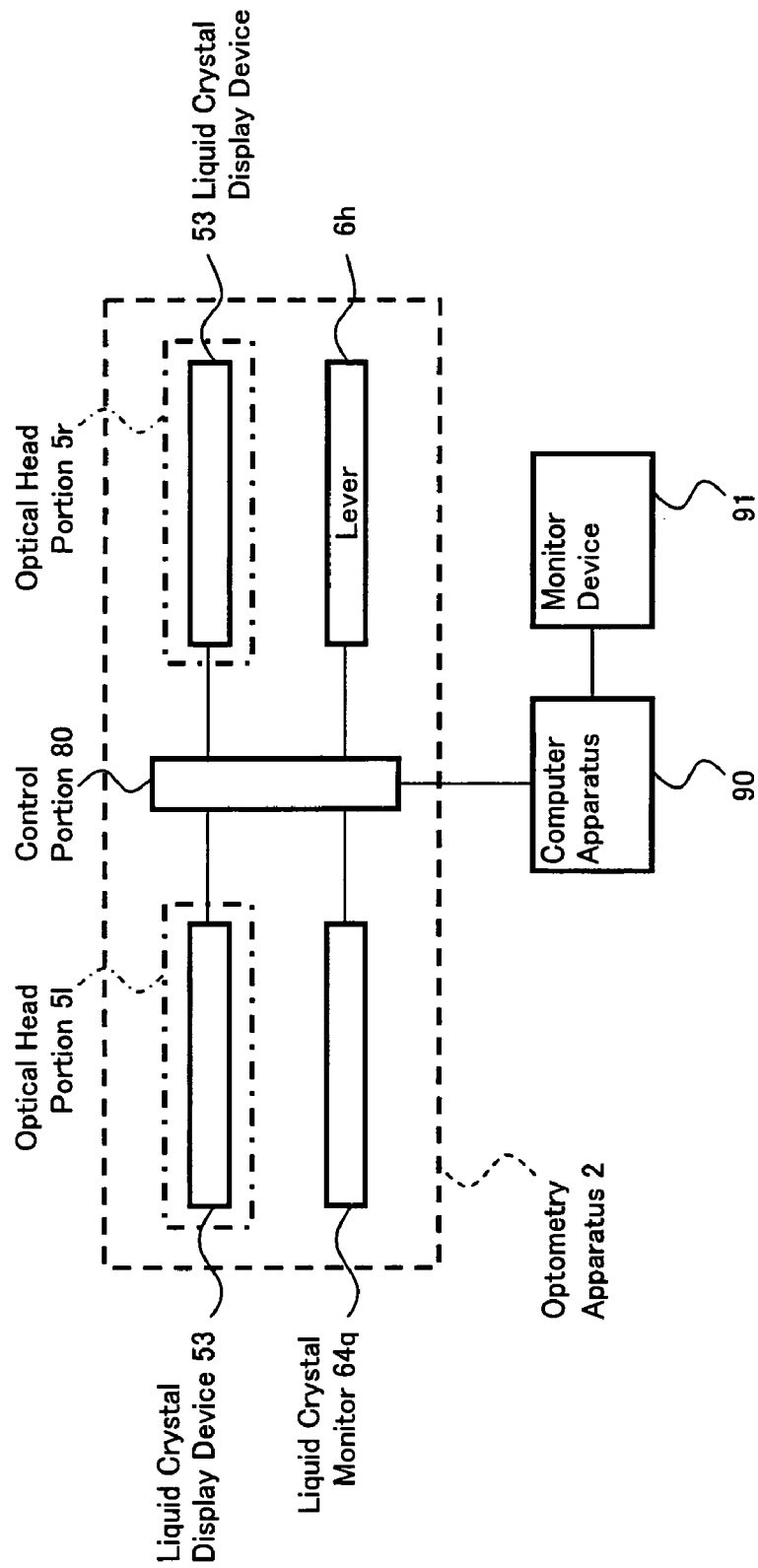
FIG. 12 is a schematic block diagram showing an example of a control system included in the optometry apparatus according to the first embodiment of the present invention.
Figure 13:
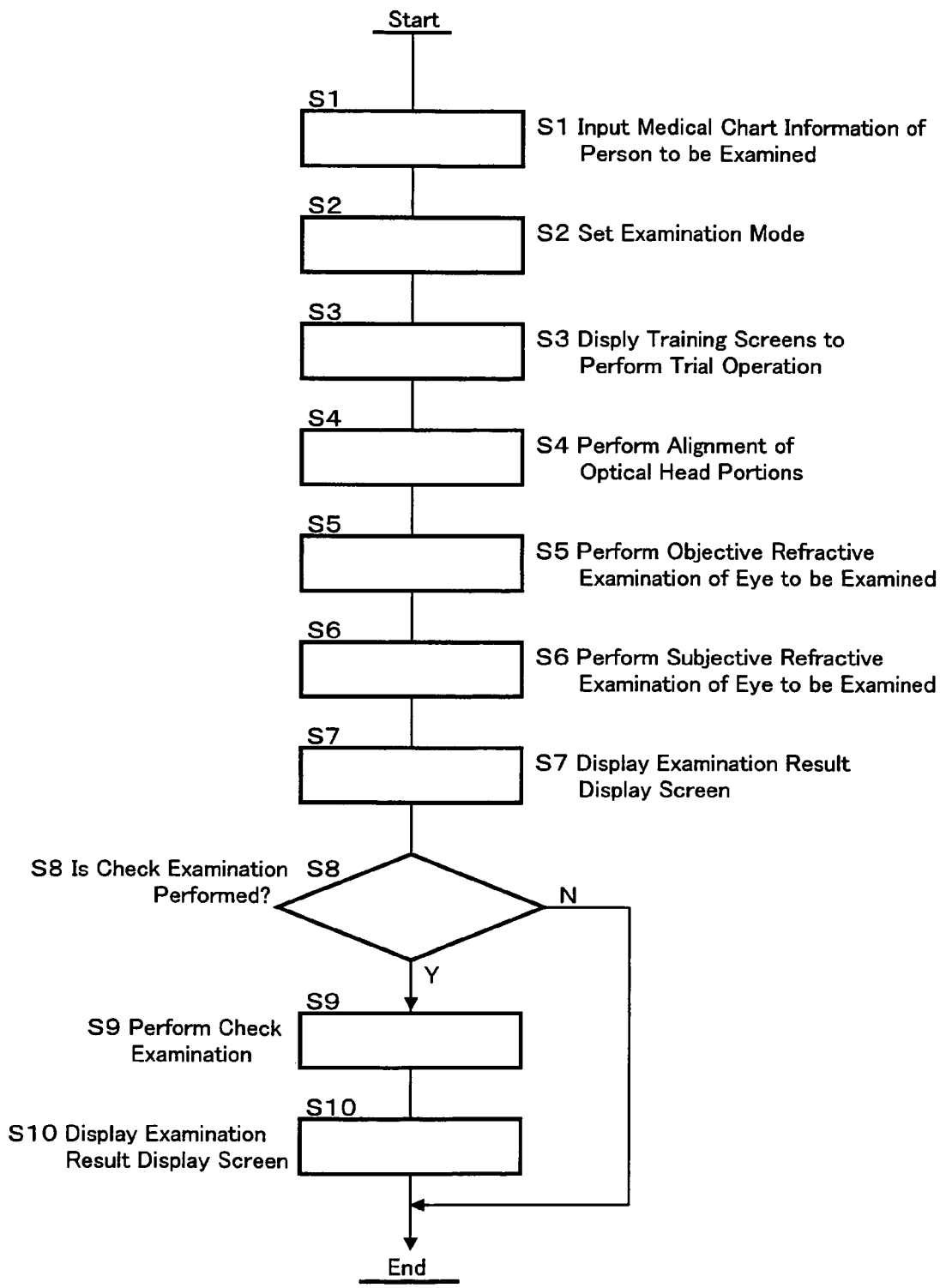
FIG. 13 is a flow chart showing an example of an examination procedure executed by the optometry apparatus according to the first embodiment of the present invention.
Figure 14:
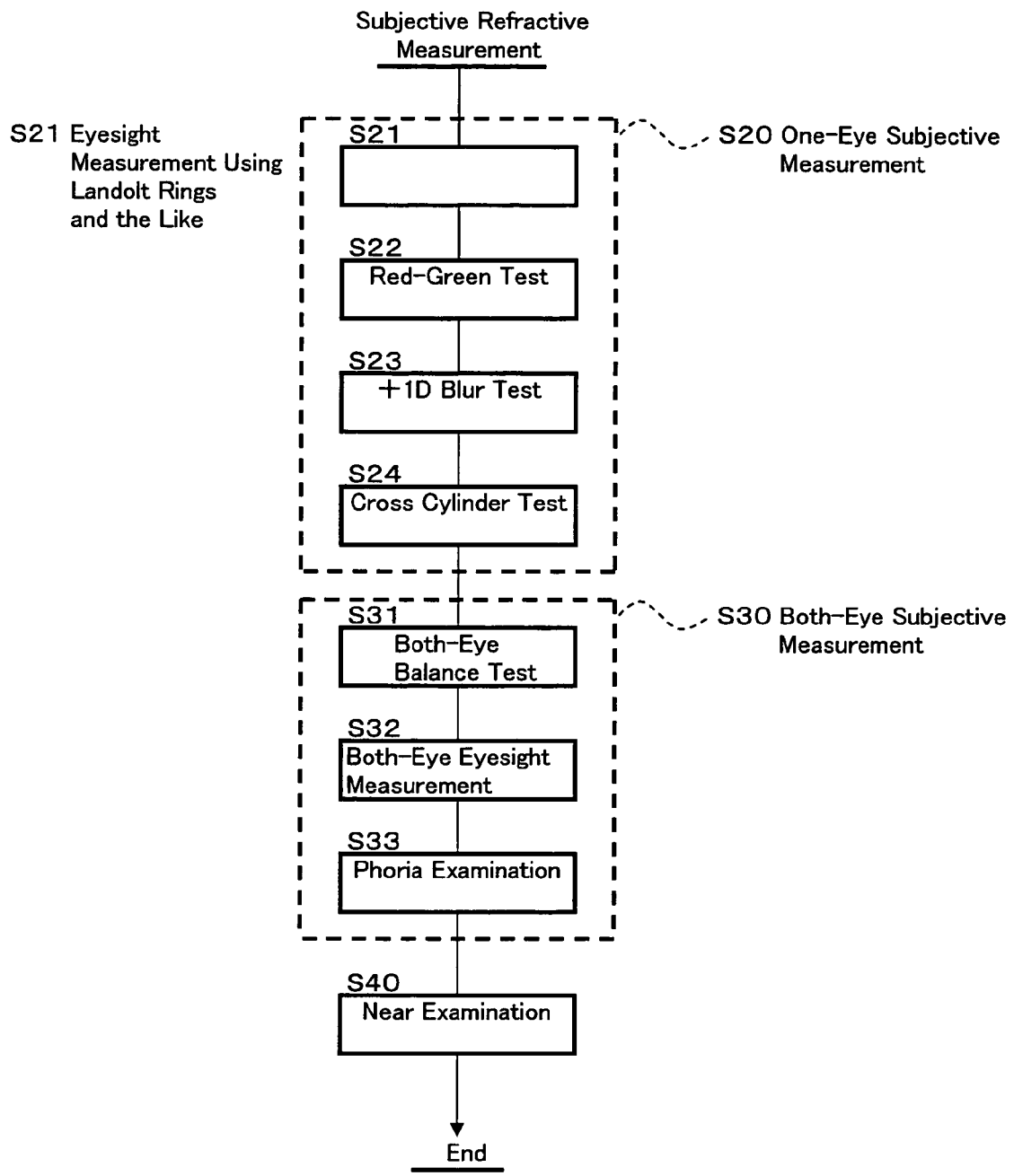
FIG. 14 is a flow chart showing an example of the examination procedure executed by the optometry apparatus according to the first embodiment of the present invention.

FIG. 1 is an external side view showing a structure of an optometry apparatus according to a first embodiment of the present invention and FIG. 2 is an external perspective view showing the optometry apparatus. FIGS. 3 to 11 show a structure of an optical system housed in the optometry apparatus. FIG. 12 is a block diagram showing a control system of the optometry apparatus. FIGS. 13 and 14 are flow charts showing an optometry procedure performed by the optometry apparatus. FIGS. 15 to 21 show display patterns of images indicated to a person to be examined.

Hereinafter, a schematic structure such as an outline, of the optometry apparatus according to this embodiment will be first described. Next, the structure of the optical system will be described. Subsequently, the control system of the optometry apparatus will be described and then the flow of the optometry procedure will be described.

[Structure of Optometry Apparatus]

As shown in FIG. 1, an optometry apparatus 2 to be used is placed on an optometry table 1 whose height is adjustable. A person to be examined 4 performs an examination in sitting on an optometry chair 3 located together with the optometry table 1.

As shown in FIG. 2, a pillar 64s elected on the optometry table 1. A liquid crystal monitor 64q is provided in an upper end of the pillar 64s. Note that a structure in which the liquid crystal monitor 64q is not located may be employed.

As shown in FIGS. 1 and 2, the optometry apparatus 2 includes a base portion 5a, a drive mechanism box 5b provided on the base portion 5a, a pair of right and left optical head portions 5l and 5r incorporating a measurement optical system described later, and a face holding device 6 for holding the face of the person to be examined 4 during an examination. Here, it is construed that a "holding" state includes not only a state in which the face of the person to be examined 4 is completely fixed to prevent the face from moving but also a state in which the face is allowed to move within a range in which an eye to be examined can be measured by the optical head portions 5*l* and 5*r*. The optical head portions 5*l* and 5*r* are supported on pillars 5*p* and 5*q* and separately driven in the three-dimensional directions by a drive mechanism box 5*b*. A liquid crystal monitor 64*l* is provided on a front surface of the optical head portion 5*l* and a liquid crystal monitor 64*r* is provided on a front surface of the optical head portion 5*r*. An anterior segment image of the eye to be examined, an eye fundus reflection image thereof, and the like, which are obtained during the examination are displayed on each of the liquid crystal monitors 64*l* and 64*r*. An examiner or an assistant (referred to as an operator) can recognize whether or not the person to be examined 4 properly performs the examination based on the displayed anterior segment image.

The face holding device 6 has a pair of right and left pillars 6*a* and 6*b*, a forehead support 6*c* supported by a member connected with upper ends of the pillars 6*a* and 6*b*, and a chin rest 6*d* located under the forehead support 6*c*, which are provided therein. The forehead support 6*c* is a member in contact with the forehead of the person to be examined 4 during the examination. The forehead support 6*c* is formed in an arc shape to improve the contact with the forehead and the position thereof is adjustable in frontward and backward directions. The chin rest 6*d* is a member on which the person to be examined 4 rests the chin during the examination and the position thereof is adjustable in upward and downward directions by a pair of right and left knobs 6*e*. In order to perform the examination, the person to be examined 4 rests the chin on the chin rest 6*d* and brings the forehead into contact with the forehead support 6*c*, with the result that the face is held.

The drive mechanism box 5*b* includes a XYZ drive mechanism for separately driving the pillars 5*p* and 5*q* in the three-dimensional directions. Although the detailed structure of the XYZ drive mechanism is not shown, it is possible to employ, for example, a known structure having a pulse motor and a feed screw. Therefore, the pillars 5*p* and 5*q*, that is, the optical head portions 5*l* and 5*r* are separately driven in the three-dimensional directions.

The drive mechanism box 5*b* further includes a rotation drive mechanism for rotating separately driving the pillars 5*p* and 5*q* in the lateral direction, which is provided therein. It is possible to employ a known structure having a pulse motor and a feed screw. A structure in which a pulse motor and gears for transferring the torque of the pulse motor to the pillars 5*p* and 5*q* are combined with one another can be employed for the rotation drive mechanism. Note that the rotation drive mechanism rotates the pillars 5*p* and 5*q*, that is, the optical head portions 5*l* and 5*r* about eyeball rotational points of the right and left eyes of the person to be examined 4 in directions reverse to each other.

Each of the optical head portions 5*l* and 5*r* houses various optical systems described later as shown in FIGS. 3 to 7. In the optical head portions 5*l* and 5*r*, the respective optical systems is operated to simultaneously perform objective refraction measurement and subjective refraction measurement on both eyes of the person to be examined 4.

A joystick lever (hereinafter may be merely referred to a lever) 6*h* is provided on the base portion 5*a*. The lever 6*h* can be tilted, for example, in eight directions such as the up direction, the down direction, the right direction, the left direction, the upper right direction, the upper left direction, the lower right direction, and the lower left direction. The lever 6*h* may be tilted in four directions such as the up direction, the down direction, the right direction, and the left direction. A button 6*g* is provided on an upper portion of the lever 6*h*. The person to be examined 4 operates the lever 6*h* and the button 6*g* to perform the examination.

(Structure of Optical System)

Figure 3:
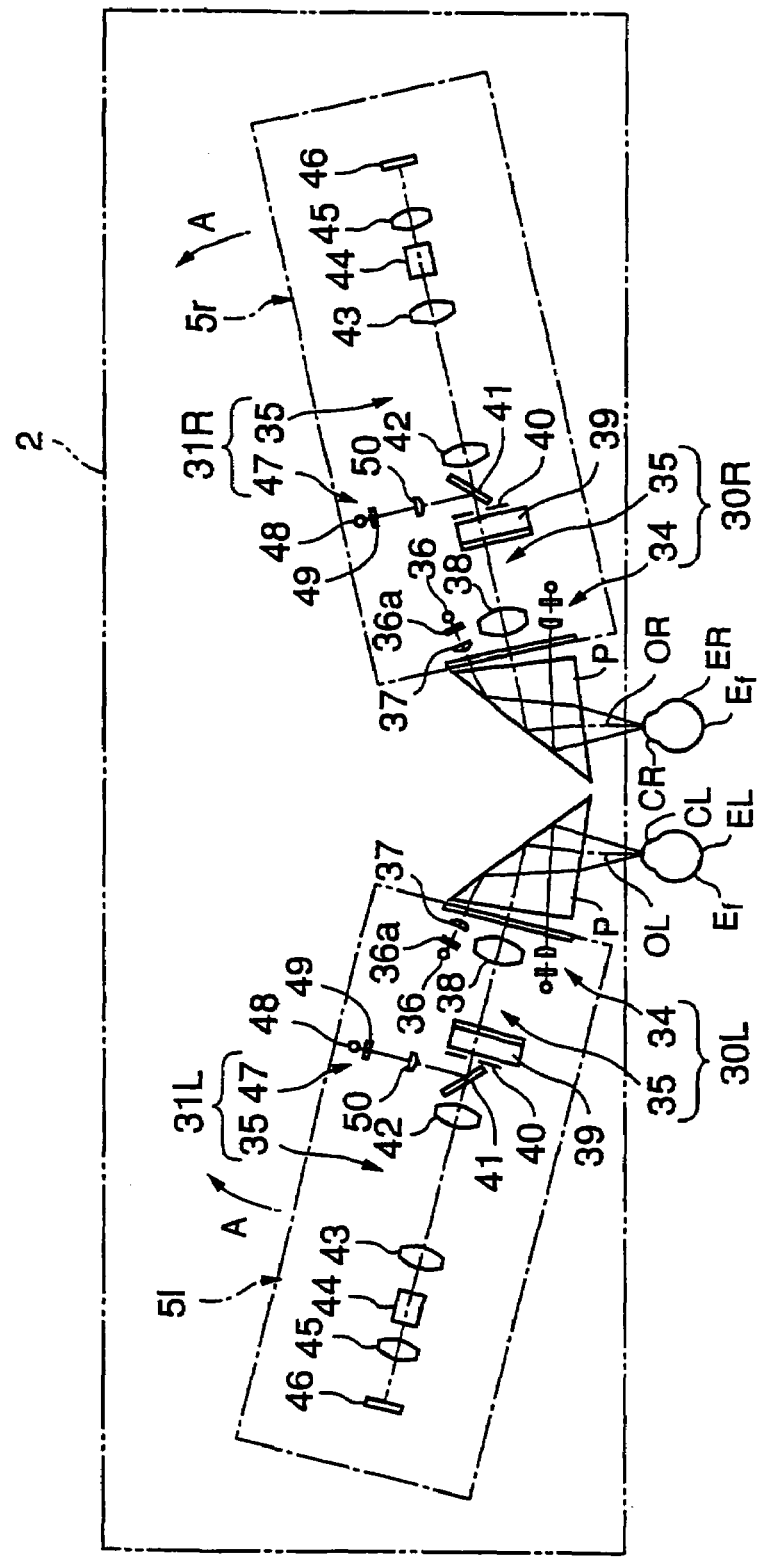
FIG. 3 is a schematic view showing an example of a structure of a measurement optical system included in the optometry apparatus according to the first embodiment of the present invention.
Figure 4:
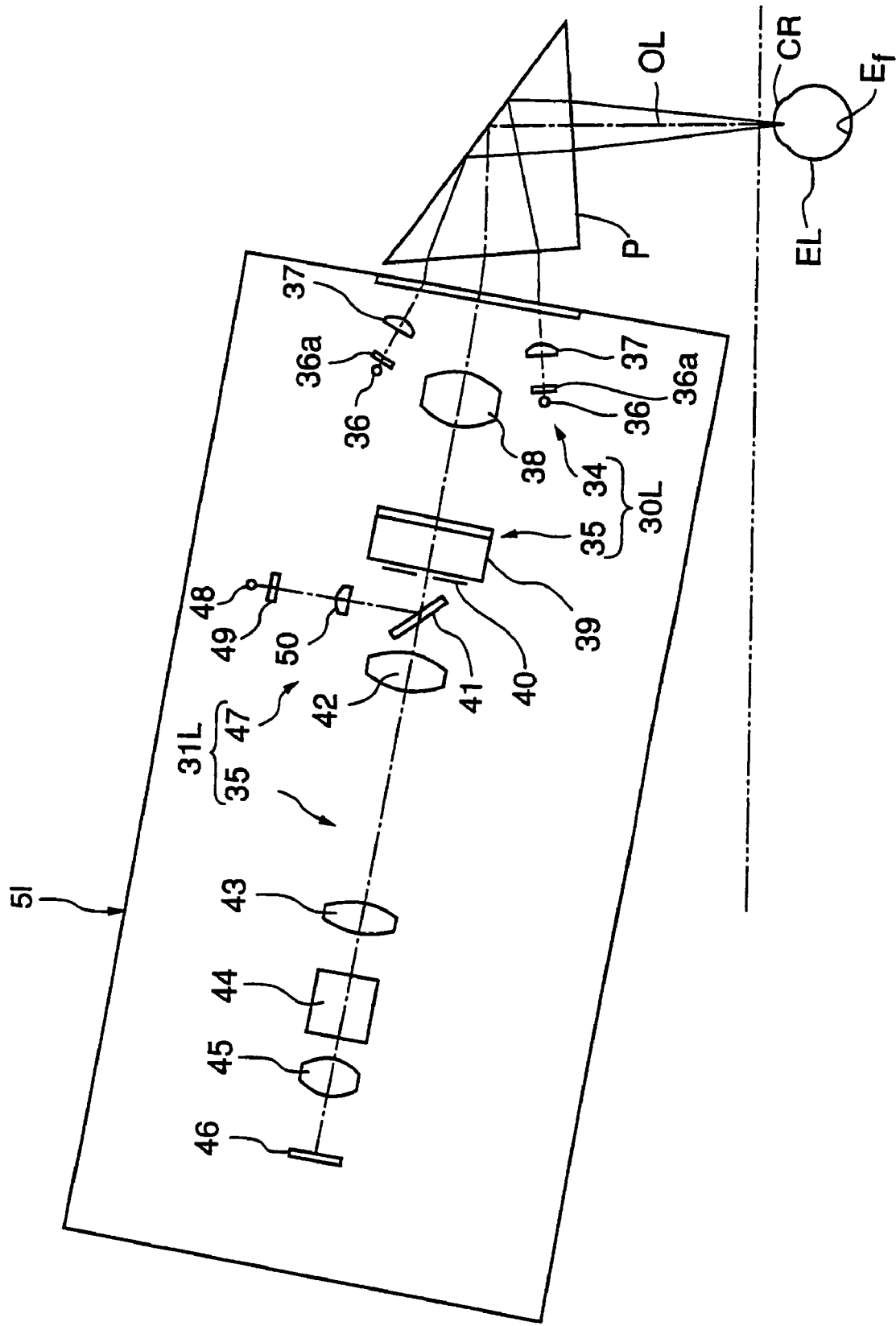
FIG. 4 is a schematic view showing an example of the structure of the measurement optical system included in the optometry apparatus according to the first embodiment of the present invention.
Figure 5:
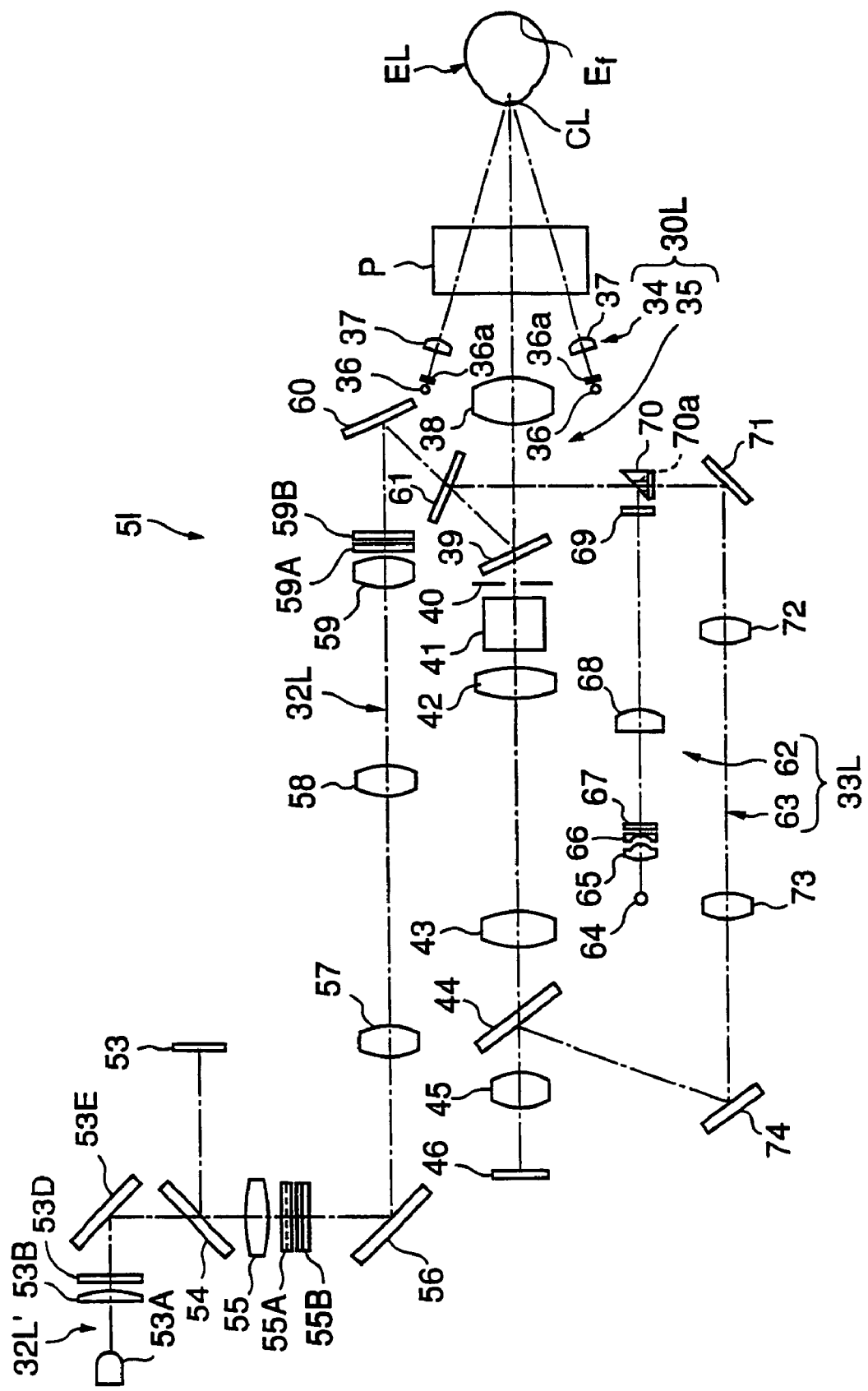
FIG. 5 is a schematic view showing an example of the structure of the measurement optical system included in the optometry apparatus according to the first embodiment of the present invention.
Figure 6:
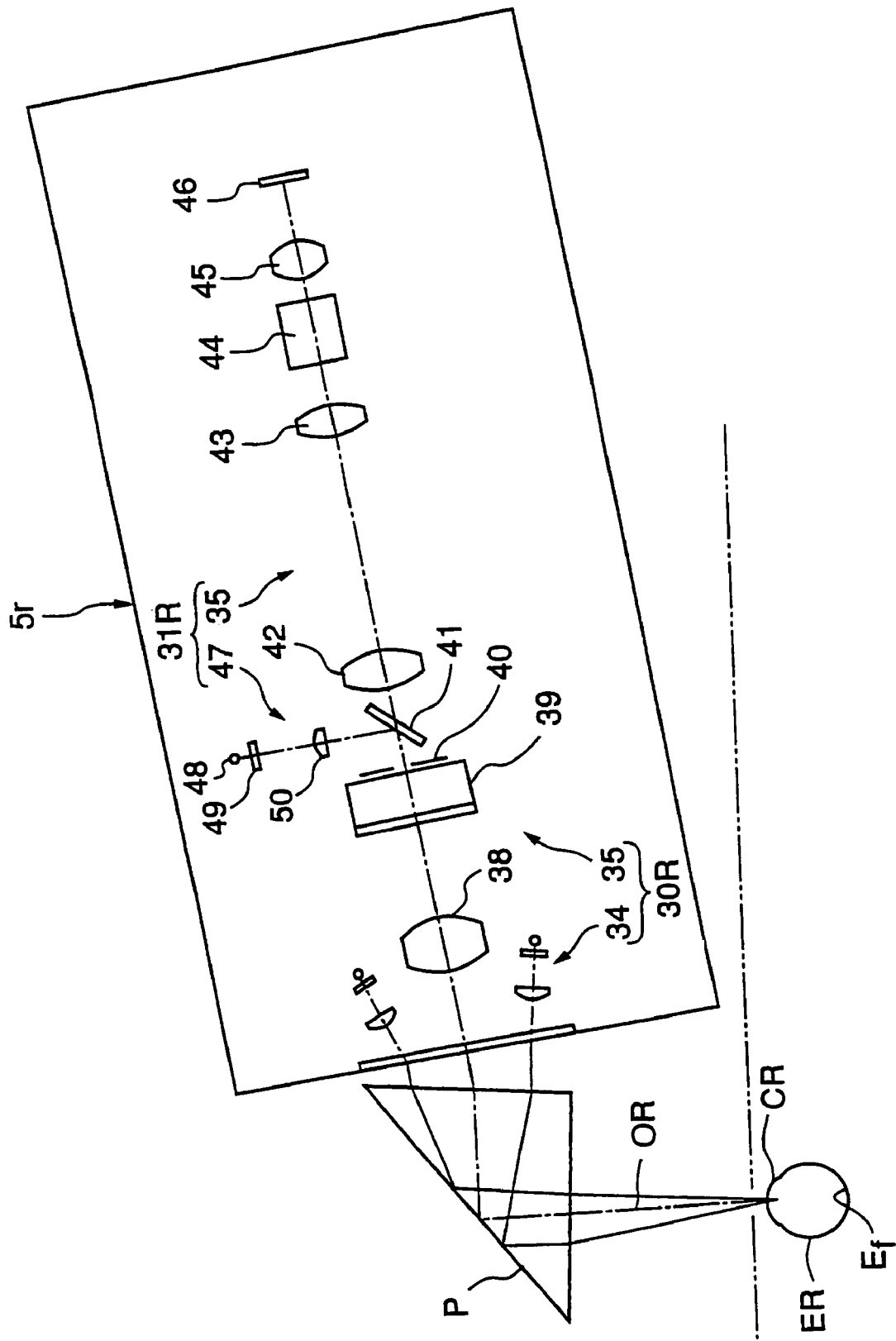
FIG. 6 is a schematic view showing an example of the structure of the measurement optical system included in the optometry apparatus according to the first embodiment of the present invention.
Figure 7:
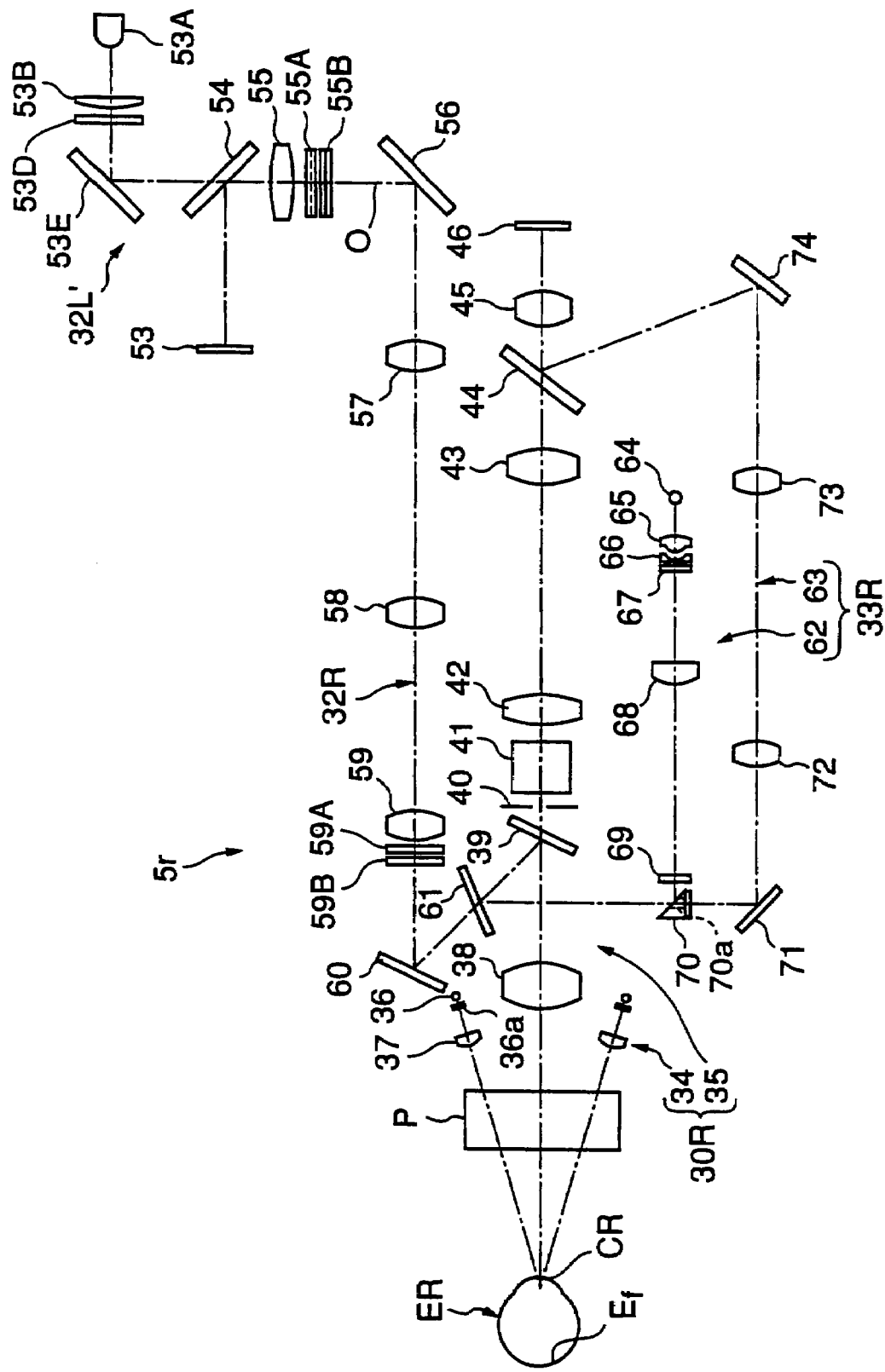
FIG. 7 is a schematic view showing an example of the structure of the measurement optical system included in the optometry apparatus according to the first embodiment of the present invention.

Structures of measurement optical systems for measuring refractive powers of the right and left eyes of the person to be examined 4, which are housed in the optical head portions 5*l* and 5*r* will be described in detail. First, a measurement optical system for measuring refractive power of the left eye of the person to be examined 4 is housed in the optical head portion 5*l*. As shown in FIGS. 3 to 5, this measurement optical system includes an anterior segment image taking optical system 30L, an XY-alignment optical system 31L, a fixation optical system 32L, and a refractive power measurement optical system 33L. Similarly, a measurement optical system for measuring refractive power of the right eye of the person to be examined 4 is housed in the optical head portion 5*r*. As shown in FIGS. 3, 6, and 7, this measurement optical system includes an anterior segment image taking optical system 30R, an XY-alignment optical system 31R, a fixation optical system 32R, and a refractive power measurement optical system 33R. The measurement optical system of the optical head portion 5*l* for left eye measurement and the measurement optical system of the optical head portion 5*r* for right eye measurement are symmetrically disposed. Hereinafter, the measurement optical system of the optical head portion 5*l* for left eye measurement will be described unless otherwise specified.

The anterior segment image taking optical system 30L provided in the optical head portion 5*l* is composed of an anterior segment illumination optical system 34 and an image taking optical system 35.

As shown in FIGS. 4, and 5, the anterior segment illumination optical system 34 includes light sources 36 for illuminating the anterior segment of the left eye of the person to be examined 4 (eye to be examined EL), diaphragms 36*a* for limiting cross sectional areas of light fluxes emitted from the light sources 36, and projection lenses 37 for projecting the light fluxes passing through the diaphragms 36*a* to the anterior segment of the eye to be examined EL.

The image taking optical system 35 includes a prism P, an objective lens 38, a dichroic mirror 39, a diaphragm 40, a dichroic mirror 41, relay lenses 42 and 43, a dichroic mirror 44, a CCD 46, and a CCD lens 45 for imaging a light flux on a light receiving surface of the CCD 46. Reflection light on the anterior segment of the eye to be examined EL illuminated by the anterior segment illumination optical system 34 is incident on the prism P. A light flux reflected on a reflective surface of the prism P is incident on the objective lens 38.

The XY-alignment optical system 31L is an optical system for aligning the measurement optical system of the optical head portion 5*l* with the eye to be examined EL in X- and Y-directions. The XY-alignment optical system 31L is composed of an alignment illumination optical system 47 for projecting an alignment light flux to the eye to be examined EL and the image taking optical system 35 for receiving reflection light on the eye to be examined EL, serving as an alignment light receiving optical system. Assume that the right-and-left direction as viewed from the person to be examined 4 is an X-direction and the up-and-down direction as viewed from the person to be examined 4 is a Y-direction. In addition, assume that the depth direction of the optometry apparatus 2 as viewed from the person to be examined 4 is a Z-direction.

As shown in FIGS. 3 and 4, the alignment illumination optical system 47 includes an illumination light source 48 for emitting a light flux for alignment in the X- and Y-directions, a diaphragm 49 for alignment index, a relay lens 50, the dichroic mirror 41, the diaphragm 40, the dichroic mirror 39, the objective lens 38, and the prism P.

The fixation optical system 32L includes a liquid crystal display device 53 for displaying various indices (charts), a half mirror 54 for reflecting light from the liquid crystal display device 53, a collimator lens 55, rotary prisms 55A and 55B for adjusting prism power and a prism base direction in a phoria examination, and a reflective mirror 56. The fixation optical system 32L further includes a movable lens 57 used to perform, for example, fixation and fogging on the eye to be examined EL, relay lenses 58 and 59, variable cross cylinder lenses (VCC lenses) 59A and 59B for adjusting astigmatic power and an astigmatic axial angle in an astigmatic examination, a reflective mirror 60, a dichroic mirror 61, the dichroic mirror 39, the objective lens 38, and the prism P.

The liquid crystal display device 53 displays various indices for subjective eye examination, such as an eyesight chart including Landolt rings for eyesight examination, a fan chart for astigmatic measurement, a cross chart for phoria examination, and a RG chart for red-green examination (red-green (RG) test) in addition to a fixed index such as a scene chart. Patterns of these indices will be described later. Note that a known index indicating unit may be used instead of the liquid crystal display device. In the index indicating unit, various indices are provided on a turret plate and indicated to the eye to be examined EL by background illumination.

Figure 8:
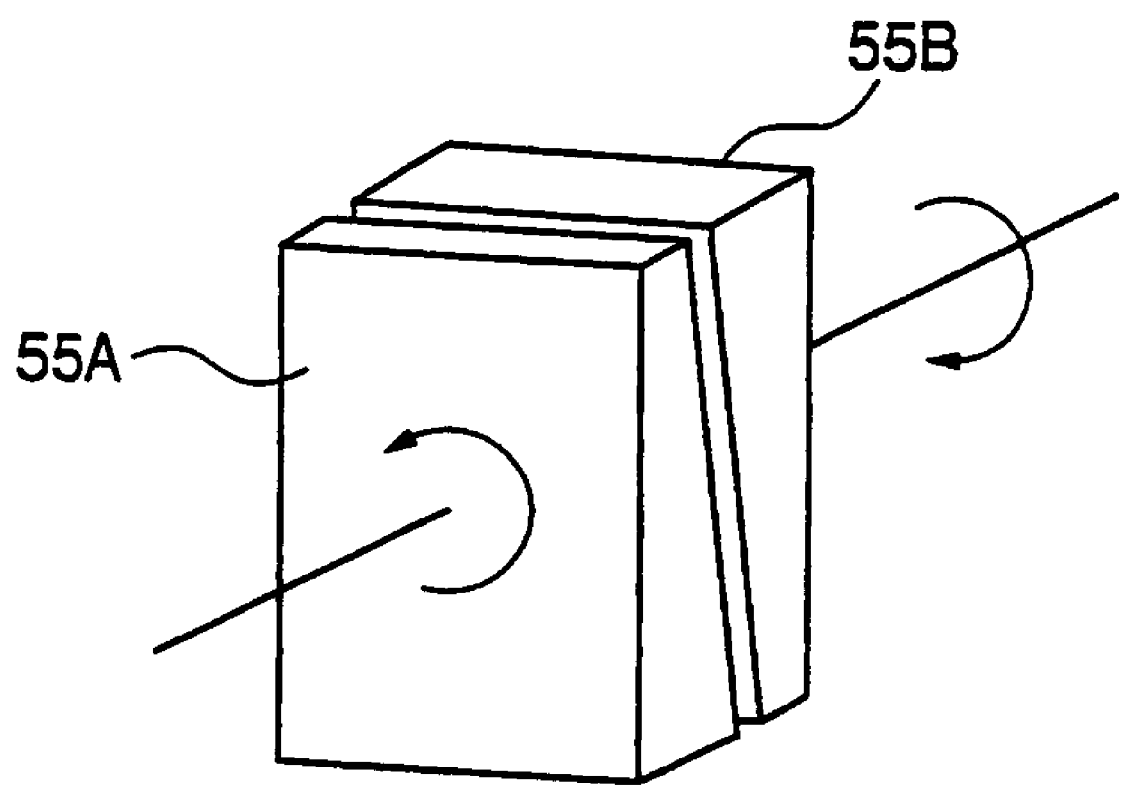
FIG. 8 is a schematic view showing an example of the structure of the measurement optical system included in the optometry apparatus according to the first embodiment of the present invention.
Figure 9:
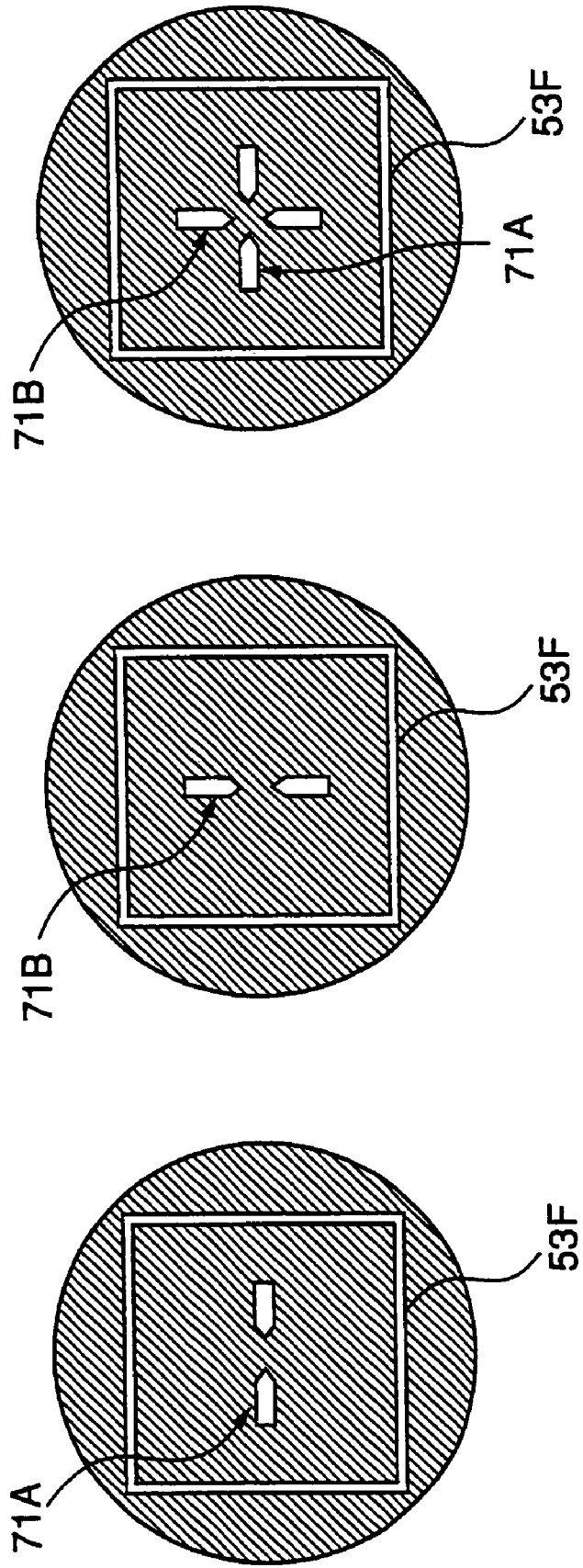

The rotary prisms 55A and 55B are separately rotated by a pulse motor or the like. As shown in FIG. 8, when the rotary prisms 55A and 55B rotate in directions reverse to each other, the prism power continuously changes. On the other hand, when the rotary prisms 55A and 55B integrally rotate in the same direction, the prism base direction continuously changes.

When the cross chart is indicated to the eye to be examined to perform a phoria examination, an index 71A shown in FIG. 9A is displayed on the liquid crystal display device 53 of the optical head portion 5l to indicate the index 71A to the left eye to be examined EL. Simultaneously, an index 71B shown in FIG. 9B is displayed on the liquid crystal display device 53 of the optical head portion 5r to indicate the index 71B to a right eye to be examined ER. When each of the eyes to be examined EL and ER is a normal eye, as shown in FIG. 9C, the index 71A and the index 71b are normally fused with each other. Therefore, the indices for right and left eyes cross each other at the center. However, when the eye to be examined has phoria, the indices for right and left eyes cross each other at a position deviated from the center. When the damage to the eye to be examined is severe, the person to be examined visually recognizes that the indices for right and left eyes do not cross each other by deviation. Thus, the rotary prisms 55A and 55B are rotated to measure the prism power and the prism base direction when the indices 71A and 71B for right and left eyes are viewed so as to cross each other at the center as shown in FIG. 9C.

Figure 10:
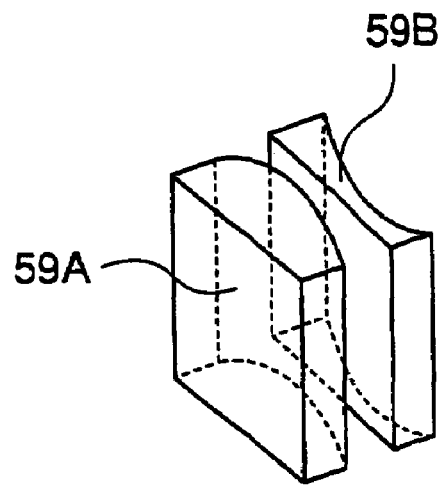
FIG. 10 is a schematic view showing an example of the structure of the measurement optical system included in the optometry apparatus according to the first embodiment of the present invention.

As shown in FIG. 10, the VCC lens 59A has a convex surface and the VCC lens 59B has a concave surface. The VCC lenses 59A and 59B are separately rotated by a pulse motor or the like. When VCC lenses 59A and 59B rotate in directions reverse to each other, astigmatic power changes. On the other hand, when the VCC lenses 59A and 59B integrally rotate in the same direction, an astigmatic axial angle changes.

The movable lens 57 is moved in an optical axis direction by a pulse motor or the like to change spherical power added to the eye to be examined EL. When the movable lens 57 is moved in the optical axis direction by a distance corresponding to the refractive power of the eye to be examined EL, the operator can perform the fixation and fogging on the eye to be examined EL.

As shown in FIG. 5, a fusion index indicating optical system 32L' is provided on an optical path of light passing through the half mirror 54 of the fixation optical system 32L. The fusion index indicating optical system 32L' includes an LED 53A for emitting illumination light, a collimator lens 53B, a fusion frame chart 53D, and a total reflection mirror 53E. As shown in FIG. 11, the fusion frame chart 53D has a square frame transmission window (fusion window) 53F and light shielding portions 53G, which are formed therein. The collimator lens 53B has a diffusing surface provided thereon. The fusion frame chart 53D is uniformly illuminated with light from the LED 53A. When the examination is performed with a state in which both eyes are open, the fusion frame 53F is indicated if necessary and acts as a fusion stimulation index for aiding the fusion of the left and right eyes to be examined EL and ER.

In this embodiment, the fusion index indicating optical system 32L' is associated with the fixation optical system 32L. When the fusion frame 53F is displayed on the liquid crystal display device 53, the fusion index indicating optical system 32L' maybe integrally constructed with the fixation optical system 32L. The fusion index indicating optical system 32L' may be completely separated from the fixation optical system 32L.

As shown in FIG. 5, the refractive power measurement optical system 33L is composed of a measurement light flux projecting optical system 62 for projecting a light flux for objective measurement to the eye to be examined EL and a measurement light flux receiving optical system 63 for receiving reflection light of the projected light flux on the eye to be examined EL.

The measurement light flux projecting optical system 62 includes a measurement light source 64 such as an infrared LED, a collimator lens 65, a cone prism 66, a ring index 67, a relay lens 68, a ring diaphragm 69, a holed prism 70 in which a transmission hole 70a is formed at the center, the dichroic mirrors 61 and 39, the objective lens 38, and the prism P.

The measurement light flux receiving optical system 63 includes the prism P which is incident on reflection light on an eye fundus Ef of the eye to be examined EL, the objective lens 38, the dichroic mirrors 39 and 61, the holed prism 70 having the transmission hole 70a, a reflective mirror 71, a relay lens 72, a movable lens 73, a reflective mirror 74, the dichroic mirror 44, the CCD lens 45, and the CCD 46.

(Structure of Control System)

Next, a structure of a control system of the optometry apparatus 2 according to this embodiment will be described with reference to a block diagram shown in FIG. 12.

The control system of the optometry apparatus 2 is composed of a control portion 80 for controlling respective portions of the apparatus, serving as a main component. The control portion 80 is housed in, for example, the base portion 5a of the optometry apparatus 2 and includes a nonvolatile storage device (for example, a ROM) and an arithmetic and control device (for example, a CPU). The nonvolatile storage device stores software including control programs for executing an examination procedure described later. The arithmetic and control device executes the software to control the respective portions of the apparatus.

The control portion 80 controls respective parts of the optical head portions 5*l* and 5*r*. In particular, the control portion 80 controls the liquid crystal display devices 53 of the fixation optical systems 32L and 32R in the optical head portions 5*l* and 5*r*. Note that the liquid crystal display devices 53 (and the fixation optical systems 32L and 32R for projecting display contents thereof to the eyes to be examined EL and ER) compose "index indicating means" and "display means" in the present invention. Although not shown, the control portion 80 controls the movable lens 57, the VCC lenses 59A and 59B, the rotary prisms 55A and 55B, the light sources 36, the illumination light source 48, the LED 53A, and the like. In addition, the control portion 80 executes, for example, digital processing on an image taken by the CCD 46. The control portion 80 controls the XYZ drive mechanism housed in the drive mechanism box 5*b* to move the optical head portions 5*l* and 5*r*.

The control portion 80 performs display control of the liquid crystal monitor 64*q*. The display control is executed according to the control programs.

When the person to be examined 4 operates the joystick lever 6*h*, the control portion 80 controls respective parts of the optometry apparatus 2, such as the optical head portions 5*l* and 5*r* according to the control programs based on operational details thereof. The joystick lever 6*h* composes "operating means" in the present invention. Note that all operating devices including a pointing device such as a mouse or a track ball can be used for the "operating means" in the present invention. The operating means may be directly provided in the optometry apparatus 2 or provided in a computer apparatus (for example, the computer apparatus 90 shown in FIG. 12) connected with the optometry apparatus 2.

The optometry apparatus 2 is connected with the computer apparatus 90 through a network such as a LAN. The computer apparatus 90 is used as a console for person to be examined in the optometry apparatus 2. The computer apparatus 90 collects results obtained by the examination in the optometry apparatus 2. A CPU and a storage device of the computer apparatus 90 may be used for the control portion 80.

The computer apparatus 90 is connected with a monitor device 91. Various screens for controlling the operation of the optometry apparatus 2, various screens for showing results obtained by the examination, and the like are displayed on the monitor device 91. Information related to operational details (described later) to be displayed on the monitor device 91 is controlled by the control portion 80.

[Examination Procedure]

An example of an examination procedure executed by the optometry apparatus 2 having the structure described above will be described with reference to flow charts shown in FIGS. 13 and 14. FIG. 13 shows a brief examination procedure and FIG. 14 shows a subjective refractive measurement procedure included in the examination procedure. FIGS. 15 to 21 show schematic screens displayed for the person to be examined 4 by the optometry apparatus 2 during the subjective refractive measurement.

A brief examination procedure performed by the optometry apparatus 2 will be described with reference to the flow chart shown in FIG. 13. First, medical chart information such as an ID and a name of the person to be examined 4 are inputted to the optometry apparatus 2 (Step S1). With respect to a medical chart information inputting method, an operator may operate the computer apparatus 90 to input the information on a predetermined person-to-be-examined information input screen (not shown). Alternatively, a card reader may be provided for the optometry apparatus 2. An ID card of the eye to be examined 4 is read by the card reader to input the information.

Next, an examination mode is set (Step S2). An examination mode for performing a series of all examinations including objective and subjective refractive examinations and a check examination such as a provisional frame examination is set to, for example, a person on which a first examination is to be performed. An examination mode for performing only the check examination with skipping a refractive examination is set to a person on which the refractive examination is completed. In addition to those examination modes, various examination modes can be set as appropriate.

When an examination mode is set, training screens for performing trial operation in objective refractive measurement, subjective refractive measurement, and the check examination are indicated to the person to be examined 4. The person to be examined 4 performs trial optometry input operation based on the training screens (Step S3). The training screens are displayed on the liquid crystal display devices 53 of the optical head portions 5*l* and 5*r* and projected to the eyes to be examined EL and ER by the fixation optical systems 32L and 32R. Therefore, the trial input operation using the optometry apparatus 2 is performed with a state in which the person to be examined 4 looks in the optical head portions 5*l* and 5*r*.

After the trial input operation is completed, the person to be examined 4 is requested so as to hold the face to the face holding device 6. That is, the person to be examined 4 is prompted so as to rest the chin on the chin rest 6*d* and bring the forehead into contact with the forehead support 6*c*. Such processing may be performed by guide announcement or the instructions of the operator to the person to be examined 4. When the face, of the person to be examined 4 is suitably held by the face holding device 6, the optometry apparatus 2 performs positioning of the optical head portions 5*l* and 5*r* to the face of the person to be examined 4, that is, alignment processing (Step S4).

The alignment processing includes XY-directional alignment for aligning the optical axes of the optical head portions 5*l* and 5*r* with the eyes to be examined EL and ER and Z-directional alignment for adjusting the focuses of the measurement optical systems of the optical head portions 5*l* and 5*r* to the eyes to be examined EL and ER. The XY-directional alignment is automatically executed by the XY-alignment optical systems 31L and 31R and the XYZ drive mechanism housed in the drive mechanism box 5*b* under the control of the control portion 80. In order to automatically execute, the Z-directional alignment, the control portion 80 controls the XYZ drive mechanism to move the optical head portions 5*l* and 5*r* in directions of optical axes OL and OR (for example, see FIG. 3), that is, in the frontward and backward directions such that a spot image on the CCD 46 becomes clear.

When the positions of the optical head portions 5*l* and 5*r* are determined by the alignment processing, a distance between the optical axes OL and OR is just calculated. The distance between the optical axes. OL and OR is stored as a PD value (pupillary distance) of the left and right eyes to be examined EL and ER in the storage device of the control portion 80 or the storage device of the computer apparatus 90.

When the alignment processing of the optical head portions 5*l* and 5*r* is completed, the optometry apparatus 2 shifts to the refractive examination of the eyes to be examined EL and ER. In the refractive examination, first, objective refractive measurement is performed to obtain objective values of the eyes to be examined EL and ER (Step S5). Then, subjective refractive measurement is executed based on the objective values to obtain subjective values of the eyes to be examined EL and ER (Step S6). After the completion of the refractive examination, an examination result display screen (not shown) including the obtained objective values and the obtained subjective values of the eyes to be examined EL and ER is displayed on the monitor device 91 (Step S7).

The objective refractive measurement described in Step S5 is executed by the refractive power measurement optical systems 33L and 33R of the optical head portions 5l and 5r. The refractive power measurement optical systems 33L and 33R simultaneously measure spherical powers S, astigmatic powers C, and astigmatic axial angles A of the left and right eyes to be examined EL and ER. Those objective values are measured as in conventional measurement. The spherical powers, the astigmatic powers, and the astigmatic axial angles (objective values) are stored in the storage device of the control portion 80, the storage device of the computer apparatus 90, or the like.

When objective refractive measurement is completed, the examination is shifted to the subjective refractive measurement described in Step S6. In the optometry apparatus 2, first, the subjective refractive measurement is performed for each of the eyes. After that, the measurement is performed with a state in which both eyes are open. If necessary, a near examination is performed. The optometry apparatus 2 executes the subjective refractive measurement while the person to be examined 4 is guided by announcement or a screen. In the optometry apparatus 2, the indices,are projected to the eyes to be examined EL and ER by the fixation optical systems 32L and 32R and the examination proceeds based on a reply of the person to be examined 4 to the indices. In the optometry apparatus 2, the control portion 80 executes the above-mentioned software to automatically perform the subjective refractive measurement. Therefore, according to the optometry apparatus 2, the examination can be performed by the person to be examined 4 alone without an operator. Note that the person to be examined 4 experiences the trial the input operation in advance in Step S3, so the subjective refractive measurement can be smoothly conducted. The detailed procedure of the subjective refractive measurement performed by the optometry apparatus 2 will be described later (See FIG. 14).

After the completion of the refractive examination, the examination result display screen is displayed on the monitor device 91 (Step S7). The operator determines whether or not a check examination for checking refractive correction values of the eyes to be examined EL and ER, such as a provisional frame examination is performed (Step S8). When the check examination is not performed, (Step S8; N), the examination to the person to be examined 4 is completed. On the other hand, when the check examination is performed, (Step S8;Y), the check examination is executed (Step S9). After the completion of the check examination, the examination result display screen including a result obtained by the examination is displayed on the monitor device 91 (Step S10). Then, the examination performed by the optometry apparatus 2 is completed.

(Processing Procedure of Subjective Refractive Measurement)

The subjective refractive measurement described in Step S6 will be described with reference to a flow chart shown in FIG. 14. Various indices indicated to the person to be examined 4 during the subjective refractive measurement will be described with reference to FIGS. 15 to 21. In the one-eye subjective refractive measurement, measurement for each of the eyes with a one-eye shielding state (referred to as one-eye subjective refractive measurement; Step S20), measurement with a both-eye open state (referred to as both-eye subjective refractive measurement; Step S30), and near examination for obtaining near power (Step S40) are conducted in order. The following procedure of subjective refractive measurement is an example of an examination flow in the optometry apparatus 2. Changing of an examination order, additions of various examination details, or deletions thereof can be performed as appropriate.

(One-eye Subjective Measurement)

For example, the right eye to be examined ER and the left eye to be examined EL are subjected to the one-eye subjective measurement described in Step S20 in this order. The measurement of each of the right and left eyes to be examined ER and EL is executed based on, for example, the following steps including: (1) eyesight measurement of the eye to be examined using indices such as Landolt rings (Step S21); (2) a red-green test for measuring the spherical power of the eye to be examined with high precision (Step S22); (3) a +1D blur test which is alternatively executed in the case where the spherical power cannot be measured in the red-green test (Step S23); and (4) a cross cylinder test for measuring the astigmatic axial angle and astigmatic power of the eye to be examined (Step S24). Hereinafter, the one-eye subjective measurement of the right eye to be examined ER will be described unless otherwise specified. The measurement of the left eye to be examined EL is executed in a similar manner.

(1) Eyesight Measurement

Figure 15A:
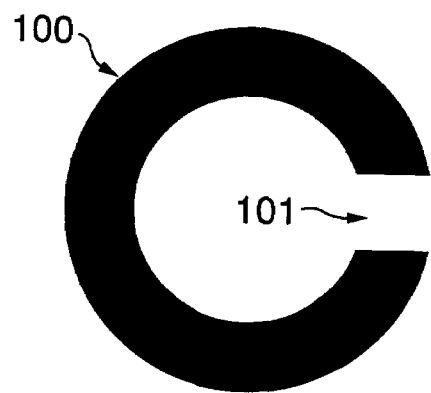

In the eyesight measurement described in Step S21, for example, an eyesight measurement index (Landolt ring 100) as shown in FIG. 15A is indicated to the person to be examined 4. When the index is to be indicated, an image of the Landolt ring 100 is displayed on the liquid crystal display device 53 of the optical head portion 5r by the control of the control portion 80 and projected to the right eye to be examined ER by the fixation optical system 32R. The indicated Landolt ring 100 has a gap 101 which is formed therein and located in any one of eight directions (an upper direction, a lower direction, a right direction, a left direction, an upper right direction, a lower right direction, an upper left direction, and a lower left direction). In the Landolt ring 100 shown in FIG. 15A, the gap 101 is formed in the right direction. Note that it is also possible to use a Landolt ring having a gap located on any one of four directions (the upper direction, the lower direction, the right direction, and the left direction).

The control portion 80 may cause the liquid crystal monitor 64q and/or the monitor device 91 to display the Landolt ring 100. When the operator views a display content of the liquid crystal monitor 64q and/or a display content of the monitor device 91, it is possible to check the detail of an examination which the person to be examined 4 is performing or an index indicated to the person to be examined 4.

The person to be examined 4 views the Landolt ring 100 indicated to the right eye to be examined ER to visually recognize the forming direction of the gap 101. Then, the person to be examined 4 operates the lever 6h to specify the recognized forming direction of the gap 101. The control portion 80 receives an input signal indicating the specified direction from the lever 6h and causes the liquid crystal display device 53 to display an arrow mark 102 indicating the direction (see FIG. 15B).

The person to be examined 4 visually recognizes the direction indicated by the displayed arrow mark 102. Therefore, it is possible to check whether or not the forming direction of the gap 101 which is recognized by the person to be examined 4 coincides with the direction indicated by the input signal inputted from the lever 6h. That is, when the person to be examined 4 determines that the recognized forming direction coincides with the inputted direction, this means that the lever 6h is correctly operated at the time of reply. When the person to be examined 4 determines that those directions are different from each other, this means that the faulty operation of the lever 6h occurs. When subsequent faulty operation occurs, the person to be examined 4 carefully operates the lever 6h. Thus, subsequent faulty operation may be reduced and smooth proceeding of the examination can be expected.

When the Landolt ring 100 is to be displayed on the liquid crystal monitor 64q and/or the monitor device 91, the control portion 80 may cause the liquid crystal monitor 64q and/or the monitor device 91 to display the arrow mark 102 based on the input information from the lever 6h. Therefore, for example, the operator can give instructions to a person to be examined who frequently performs the faulty operation or cause the person to be examined to execute the training of the input operation (Step S3) again.

The control portion 80 operates based on the control programs such that indices are successively indicated to the person to be examined 4 according to the reply (correct or incorrect) of the person to be examined 4. Therefore, the control portion 80 determines an eyesight value of the right eye to be examined ER. The control portion 80 causes the storage device thereof or the storage device of the computer apparatus 90 to store the eyesight value therein.

(2) Red-Green Test

Figure 16:
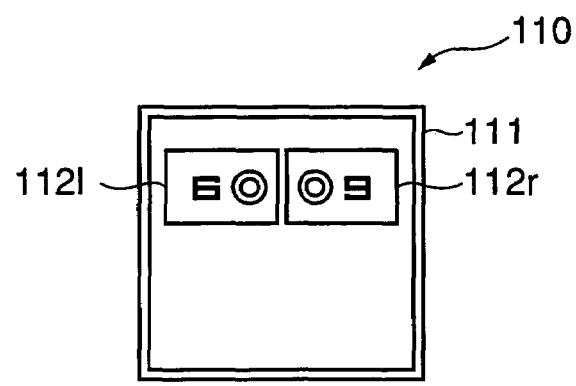
FIG. 16 is a schematic view showing an example of a display pattern of an image (red-green chart) displayed to the person to be examined by the optometry apparatus according to the first embodiment of the present invention.

In the red-green test described in Step S22, for example, an RG chart 110 as shown in FIG. 16 is indicated to the person to be examined 4. When the RG chart 110 is to be indicated, an image thereof is displayed on the liquid crystal display device 53 of the optical head portion 5r by the control of the control portion 80 and projected to the right eye to be examined ER by the fixation optical system 32R.

The RG chart 110 includes a plurality of indices located in a square frame 111. A rectangular red region 112l is formed on the left side in the frame 111 and a rectangular green region 112r is formed on the right side therein. The rectangular red region 112l has a numeral index "6" and a ring index composed of double circles, which are provided therein. The rectangular green region 112r has a numeral index "9" and a ring index identical to the ring shape of the rectangular red region 112l, which are provided therein.

The person to be examined 4 is requested by guide announce or instructions of the operator so as to compare appearance states of the red and green indices located in parallel in the lateral direction with each other and tilt the lever 6h in a corresponding direction. In reply to this, when the person to be examined 4 operates the lever 6h, an input signal generated in response to the operation is transmitted from the lever 6h to the control portion 80. The control portion 80 causes the liquid crystal display device 53 to blink a region corresponding to the tilting of the lever 6h, of the left and right rectangular regions 112l and 121r of the RG chart 110 displayed thereon based on the input signal.

For example, assume that in the case where the person to be examined 4 is requested so as to determine whether or not the numeral index "6" of the rectangular red region 112l is clearer than the numeral index "9" of the rectangular green region 112r, the person to be examined 4 determines that the numeral index "6" of the rectangular red region 112l, that is, the left side index is clear. Then, when the person to be examined 4 tilts the lever 6h to the left, the control portion 80 controls the liquid crystal display device 53 to blink the rectangular red region 112l located on the left side. If the person to be examined 4 has tilted the lever 6h to the right by faulty operation, the control portion 80 causes the liquid crystal display device 53 to blink the rectangular green region 112r located on the right side. Therefore, the person to be examined 4 can check whether or not the person performs the faulty operation.

(3) +1D Blur Test

The +1D blur test described in Step S23 is alternatively executed in the case where the red-green test cannot be adequately performed because of, for example, low understanding of the person to be examined 4. This test is based on the experimental knowledge in which an eyesight value reduces to about 0.5 to 0.7 when S+1.0D is added to objective values. More specifically, the eyesight value in which S+1.0D is added to the objective values is measured. When a result obtained by measurement is equal to an expected target eyesight value of 0.5 to 0.7, it is determined that the objective values (S, C, and A) are correct. When the measured eyesight value is smaller than 0.5, weak correction is determined. In this case, a minus D value is added until the eyesight value reaches 0.5. On the other hand, when the eyesight value exceeds 0.7, over-correction is determined. In this case, a plus D value is added until the eyesight value reduces to 0.7. Note that the target eyesight value is not limited to 0.5 to 0.7 and thus can be set to an arbitrary value.

The +1D blur test is performed using the eyesight chart such as the Landolt ring 100 shown in FIG. 15A. Even in the case of the +1D blur test, the control portion 80 causes the liquid crystal display device 53 to display the arrow mark 102 as in the case of the eyesight measurement in Step. S21. Therefore, the person to be examined 4 can check whether or not the faulty operation of the lever 6h occurs.

(4) Cross Cylinder Test

In the cross cylinder test described in Step S24, the astigmatic axial angle and astigmatic power of the eye to be examined are measured. In order to execute the cross cylinder test, the control portion 80 controls the variable cross cylinder lenses 59A and 59B to add various cylindrical powers to the eye to be examined in various directions.

The cross cylinder test is simultaneously performed for the left and right eyes to be examined EL and ER by indicating a pair of right and left dot charts (cross cylinder dot charts) to the person to be examined 4. The person to be examined 4 is requested by announce or the like so as to compare appearance states of the right and left dot charts with each other and tilt the lever 6h in a direction corresponding to a relatively clear dot chart. In reply to this, when the person to be examined 4 operates the lever 6h, an input signal generated in response to the operation is transmitted from the lever 6h to the control portion 80. The control portion 80 causes the liquid crystal display device 53 to display a frame for surrounding a dot chart corresponding to the tilting of the lever 6h, of a pair of left and right dot charts 120 and 121 displayed thereon based on the input signal.

FIG. 17A shows an example of the pair of dot charts visually recognized by the person to be examined 4. In this embodiment, the left dot chart 120 becomes a clear state and the right dot chart 121 becomes a blurred state. When the person to be examined 4 tilts the lever 6h to the left, the control portion 80 controls the liquid crystal display device 53 to display a frame 123 for surrounding the left dot chart 120 as shown in FIG. 17B. If the person to be examined 4 has tilted the lever 6h to the right by faulty operation, the flame is displayed around the right dot chart 121. Therefore, the person to be examined 4 can check whether or not the person performs the faulty operation.

FIG. 18A shows an example in which a fan chart 130 for measuring an astigmatic state of the eye to be examined is in a visual state. The fan chart 130 includes a plurality of straight portions 131, 132, 133, . . . radially arranged around a central position C as in the case of a normal fan chart. Note that FIG. 18A shows a state in which the straight portion 133 and a straight portion located symmetrical thereto visually become denser and the other straight portions visually become blurred (broken lines in FIG. 18A show blurred appearances). The fan chart 130 has twelve straight portions provided therein at intervals of 30 degrees. The number of straight portions can be set as appropriate in view of measurement accuracy and the like. The straight portions may be arranged in a semicircular shape.

The liquid crystal display device 53 displays a mark portion M together with the fan chart 130. The mark portion M rotates about the central position C on the fan chart 130 in a direction indicated by an arrow of FIG. 18A. The rotational speed of the mark portion M may be changed according to, for example, the age of the person to be examined 4. The person to be examined 4 is requested by announce or the like so as to stop the mark portion M which is rotating at a position corresponding to dense portions of the straight portions 131, 132, 133, . . . . In reply to this, the person to be examined 4 operates the lever 6h to stop the mark portion M which is rotating. When the rotation of the mark portion M is stopped, the control portion 80 obtains coordinates of a stop position of the mark portion M on the screen of the liquid crystal display device 53 and calculates an astigmatic axial angle of the eye to be examined based on the obtained coordinates. Note that the storage device of the control portion 80 stores a relationship between coordinates on the screen of the liquid crystal display device 53 and the astigmatic axial angle in advance. The control portion 80 calculates the astigmatic axial angle with reference to the stored relationship.

For example, in the case of the visual state as shown in FIG. 18A, when the mark portion M which is rotating reaches a position of the straight portion 133, the person to be examined 4 operates the lever 6h to stop the mark portion M. At this time, the fan chart becomes a display state as shown in FIG. 18B. Then, the control portion 80 calculates an astigmatic axial angle (60°) of the eye to be examined based on coordinates of the stop position, that is, coordinates (angle) of the straight portion 133. The calculated astigmatic axial angle is stored in the storage device of the control portion 80 or the storage device of the computer apparatus 90. The person to be examined 4 compares the position of a straight portion determined to be dense by the person with the stop position of the mark portion M. Therefore, the person to be examined 4 can visually check whether or not the faulty operation of the lever 6h occurs.

The mark portion M may be set to be rotatable by the lever 6h in the clockwise and counter clockwise directions. For example, when the lever 6h is tilted to the right, the control portion 80 controls such that the mark portion M rotates in the clockwise direction. When the lever 6h is tilted to the left, the control portion 80 controls such that the mark portion M rotates in the counterclockwise direction. The person to be examined 4 tilts the lever 6h to the right or the left as appropriate to stop the mark portion M at a target position of the straight portion, thereby making a reply.

While the angle and the power are added to the eye to be examined by the variable cross cylinder lenses 59A and 59B, the power in which a very dense straight portion disappears is obtained. Therefore, it is possible to obtain astigmatic power of the person to be examined. At this time, for example, the optometry apparatus 2 generates an output such as announcement for request to the person to be examined 4 such that the person presses down the button 6g provided on the upper portion of the lever 6h in the case where the dense straight portion disappears.

(Both-Eye Subjective Measurement)

After the one-eye subjective measurement is completed, the optometry apparatus 2 shifts to the both-eye subjective measurement described in Step S30. The both-eye subjective measurement is executed based on, for example, the following steps including: (1) a both-eye balance test for adjusting the subjective values obtained by the cross cylinder test of the one-eye subjective measurement (Step S31); and (2) an eyesight measurement with both-eyes (Step S32). Phoria examination may be further performed on the eyes to be examined EL and ER (Step S33). When the adequate both-eye balance test is not performed, the +1D blur test may be alternatively performed.

(1) Both-Eye Balance Test

Figure 19A:
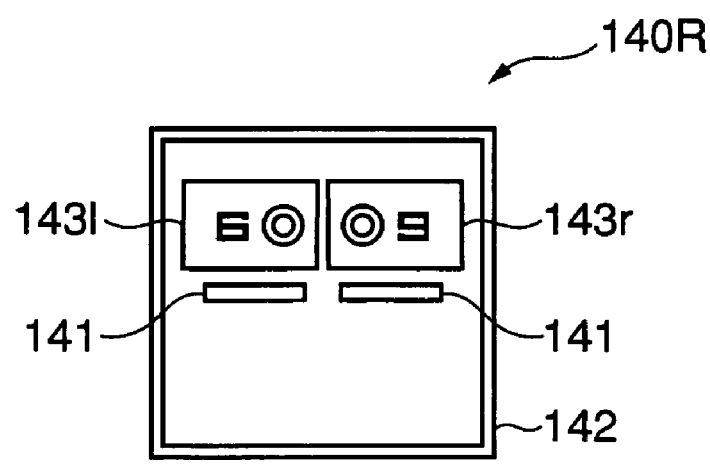
Figure 19B:
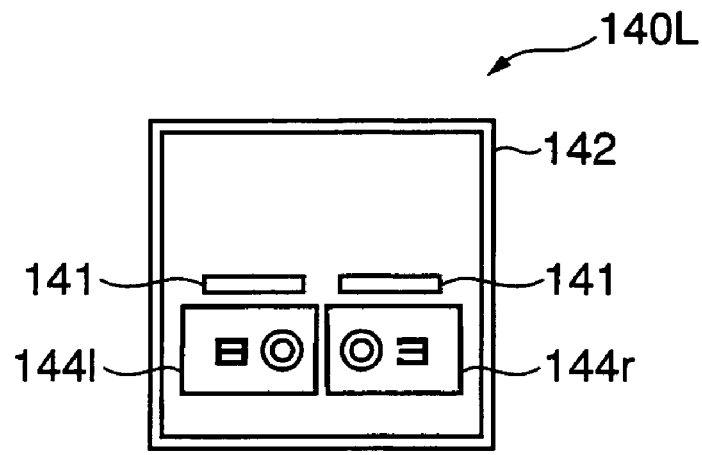
Figure 19C:
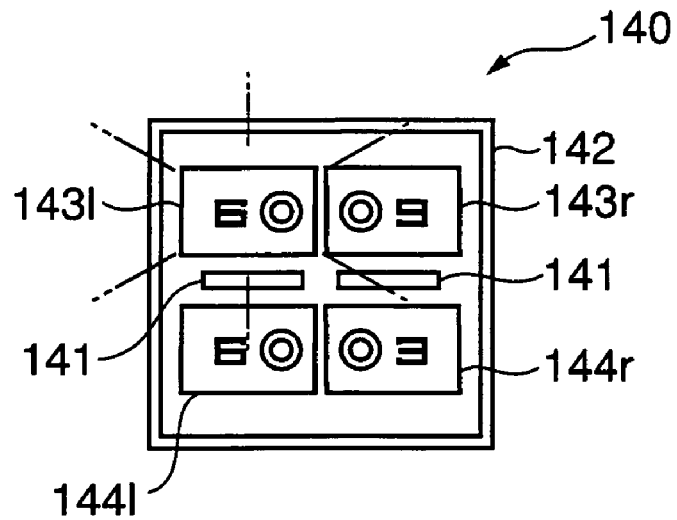

The both-eye balance test described in Step S31 is performed by indicating the RG charts as shown in FIGS. 19A and 19B to the eyes to be examined EL and ER. At this time, an RG chart 14OR as shown in FIG. 19A is displayed on the liquid crystal display device 53 of the right optical head portion 5r. In addition, an RG chart 140L as shown in FIG. 19B is displayed on the liquid crystal display device 53 of the left optical head portion 5l. Therefore, the RG chart 140R is indicated to the right eye to be examined ER and the RG chart 140L is indicated to the left eye to be examined EL. FIG. 19C shows a state of the RG chart 140 visually recognized by the person to be examined 4 when the RG chart 140R and the RG chart 140L are respectively indicated to the right and left eyes to be examined ER and EL, that is, a state in which the right RG chart 140R and the left RG chart 140L are fused and the resultant chart is visually recognized as the single RG chart 140.

As shown in FIG. 19A, the RG chart 140R indicated to the right eye to be examined ER includes a plurality of indices located in a square frame 142. A rectangular red region 143*l* is formed on the upper left side in the frame 142 and a rectangular green region 143*r* is formed on the upper right side therein. The rectangular red region 143*l* has a numeral index "6" and a ring index composed of double circles, which are provided therein. The rectangular green region 143*r* has a numeral index "9" and a ring index, which are provided therein. In addition, indices 141 that act as a fusion stimulus are provided under the rectangular regions 143*l* and 143*r*.

Similarly, in the RG chart 140L for the left eye to be examined EL as shown in FIG. 19B, a rectangular red region 144*l* is formed on the lower left side in the frame 142 and a rectangular green region 144*r* is formed on the lower right side therein. The rectangular red region 144*l* has a numeral index "8" and a ring index, which are provided therein. The rectangular green region 144*r* has a numeral index "3" and a ring index, which are provided therein. In addition, the indices 141 that act as the fusion stimulus are provided under the rectangular regions 144*l* and 144*r*.

The both-eye balance test is performed on each of the eyes to be examined with a state in which the RG charts 140*l* and 140*r* are indicated to both the eyes to be examined EL and ER. When balance adjustment is performed on the right eye to be examined ER, the control portion 80 controls the liquid crystal display device 53 of the right optical head portion 5r to blink the upper rectangular regions 143*l* and 143*r*. Then, the person to be examined 4 is requested by an output such as guide announce so as to compare appearance states of the red and green indices with each other and tilt the lever 6h in a direction corresponding to a relatively clear index. In reply to this, when the person to be examined 4 operates the lever 6h, an input signal generated in response to the operation is transmitted from the lever 6h to the control portion 80. The control portion 80 controls the liquid crystal display device 53 to blink only a rectangular region corresponding to the tilting of the lever 6h based on the input signal. For example, when the lever 6h is tilted to the left, as shown in FIG. 19C, the rectangular region 143l located on the upper left side is blinked. Here, control may be performed so as to continuously display only the rectangular region corresponding to the tilting of the lever 6h (without blinking) Alternatively, control may be performed so as to display only one rectangular region corresponding to the tilting with a state in which the other rectangular region corresponding to no tilting is not displayed. On the other hand, when balance adjustment is performed on the left eye to be examined EL, the lower rectangular regions 144l and 144r are blinked and the same examination is performed. According to the both-eye balance test, the person to be examined 4 can recognize the operational details of the lever 6h. Therefore, the person to be examined 4 can check whether or not the person performs the faulty operation.

(2) Both-Eye Eyesight Measurement

Figure 15B:
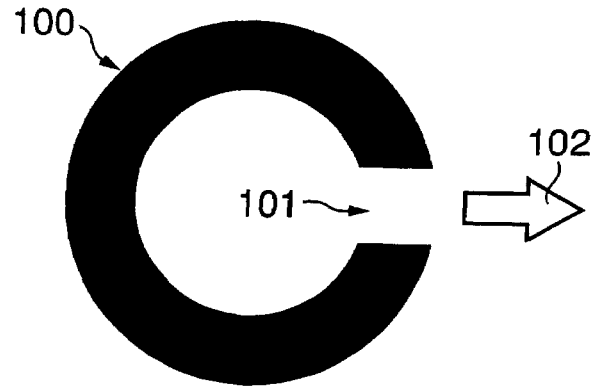

In the both-eye eyesight measurement described in Step S32, the eyesight charts such as the Landolt rings are indicated to the eyes to be examined EL and ER. The measurement is performed with a state in which the subjective values obtained by the one-eye subjective measurement are added to the eye to be examined or a naked eye state. Therefore, final subjective values are determined based on results obtained by measurement for both eyes. As shown in FIG. 15B, even in the both-eye eyesight measurement, arrow marks 102 indicating the tilt direction of the lever 6h are displayed on the liquid crystal display device 53. Thus, the person to be examined 4 can recognize the operational detail of the lever 6h to check whether or not the faulty operation occurs.

(3) Phoria Examination

In the phoria examination described in Step S33, a cross chart is used. The cross chart is composed of a pair of horizontal lines and a pair of vertical lines. The horizontal lines are indicated to only the left eye to be examined EL through a polarizing filter. The vertical lines are indicated to only the right eye to be examined ER through a polarizing filter. The horizontal lines and the vertical lines are displayed on the liquid crystal display device 53 (see FIG. 9). When the eye to be examined has no phoria, the cross chart is visually recognized in a cross shape. When there is phoria in a horizontal direction, the horizontal lines are displaced in the horizontal direction. When there is phoria in a vertical direction, the vertical lines are displaced in the vertical direction.

Figure 20A:
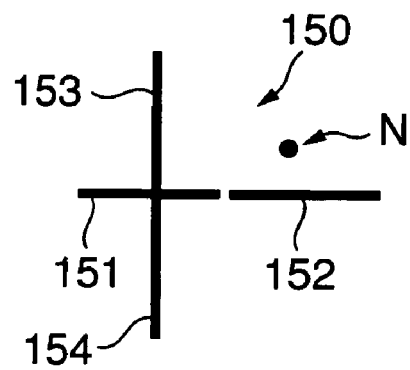

FIG. 20A shows an example of a visual recognition state of the person to be examined 4, visually recognizing the cross chart. As shown in FIG. 20A, the person to be examined 4 visually recognizes a pair of horizontal lines 15l and 152 and a pair of vertical lines 153 and 154. In this embodiment, the horizontal lines 153 and 154 are visually recognized without a change in position. The horizontal lines 151 and 152 are displaced to the right side (horizontal line 152 side). In addition to the cross chart 150, a mark N is indicated to the person to be examined 4. The mark N is two-dimensionally movable on the screen of the liquid crystal display device 53 by the operation of the lever 6h. When the one eye has suppression, only one of a group of the horizontal lines and a group of the vertical lines can be visually recognized. In the phoria examination, phoria measurement in the horizontal direction (horizontal phoria measurement) and phoria measurement in the vertical direction (vertical phoria measurement) are performed.

Figure 20B:
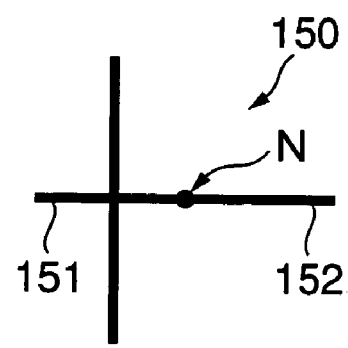

In the case of the horizontal phoria measurement, the optometry apparatus 2 outputs guide announcement or the like to make a request to the person to be examined 4 such that the person operates the lever 6h to move the mark N to a position between the two horizontal lines 151 and 152 located in the horizontal direction. As shown in FIG. 20B, When the person to be examined 4 operates the lever 6h to move the mark N to the position between the horizontal lines 151 and 152, the control portion 80 obtains the degree of horizontal phoria (prism power) based on coordinates of the mark N on the screen of the liquid crystal display device 53.

After the horizontal phoria measurement is completed, in order to perform vertical phoria measurement, the optometry apparatus 2 makes a request to the person to be examined 4 such that the person operates the lever 6h to move the mark N to a position between the two vertical lines 153 and 154 located in the vertical direction. As shown in FIG. 20B, When the person to be examined 4 operates the lever 6h to move the mark N to the position between the vertical lines 153 and 154, the control portion 80 obtains the degree of vertical phoria (prism power) based on coordinates of the mark N on the screen of the liquid crystal display device 53. Note that a relationship between the coordinates on the screen of the liquid crystal display device 53 and the prism powers in the horizontal and vertical directions is stored in advance in the storage device of the control portion 80. Therefore, the control portion 80 obtains the prism powers to the eye to be examined in the horizontal and vertical directions with reference to the stored relationship.

According to the phoria examination, the person to be examined 4 can recognize whether or not the mark N is moved to a target position. Therefore, the person to be examined 4 can check whether or not the faulty operation of the lever 6h occurs. Note that the control portion 80 composes calculation means in the present invention for calculating prism power corresponding to a predetermined position on the cross chart 150, which is specified by the operation of the level 6h by the person to be examined.

(Near Examination)

Figure 21A:
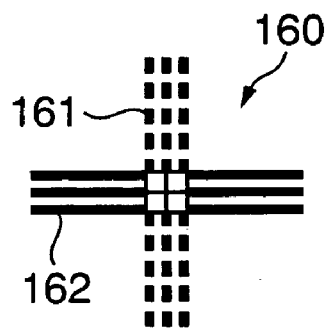

After the above-mentioned (long distance) examinations are completed, the optometry apparatus 2 shifts to near examination for measuring near power (near additional power) of each of the eyes to be examined EL and ER (Step S40). Therefore, each of the optical head portions 5l and 5r is rotated inward to converge the eyes to be examined EL and ER. Then, a near chart 160 as shown in FIG. 21A is displayed on the liquid crystal display device 53. The near chart 160 includes vertical lines 161 and horizontal lines 162. Note that FIG. 21A shows a visual state of the person to be examined 4, visually recognizing the near chart 160. Portions indicated by dot lines of FIG. 21A (vertical lines 161) means that the portions are visually recognized in a blur state.

Figure 21B:
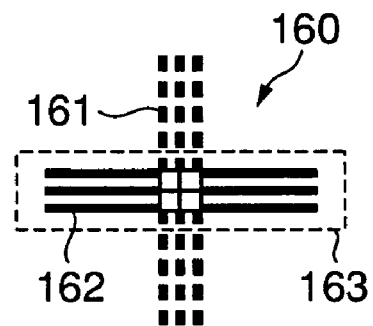

The optometry apparatus 2 generates guide announcement or the like. Therefore, the person to be examined 4 is prompted so as to compare appearance states of the vertical lines 161 and the horizontal lines 162 in the near chart 160. When the vertical lines 161 are clear, the person to be examined 4 is requested so as to operate the lever 6h upward (frontward) or downward (backward). On the other hand, when the horizontal lines 162 are clear, the person to be examined 4 is requested so as to operate the lever 6h rightward or leftward. The control portion 80 causes the liquid crystal display device 53 to display a frame for surrounding lines corresponding to the operating direction of the lever 6h. For example, as shown in FIG. 21A, in a case where the vertical lines 161 blur and the horizontal lines 162 are clear, when the lever 6h is tilted to the right or the left to select the horizontal lines 162, as shown in FIG. 21B, the control portion 80 controls the liquid crystal display device 53 to display a frame 163 surrounding the horizontal lines 162. When the lever 6h is tilted to the upper side or the lower side, a frame surrounding the vertical lines 161 is displayed.

Thus, the person to be examined 4 can recognize the operational detail of the lever 6h to check whether or not the faulty operation occurs.

[Operation and Effect]

The operation and the effect of the optometry apparatus 2 having the structure described above according to this embodiment will be described. Modified examples of the optometry apparatus 2 will be also described briefly.

According to the optometry apparatus 2, the reply of the person to be examined 4 to the various indices indicated during the subjective refractive measurement, that is, the operational detail information indicating the operational detail of the joystick lever 6h operated by the person to be examined 4 is displayed to the person to be examined 4. Therefore, the person to be examined 4 can recognize the detail of the operation performed by himself/herself to check whether or not the faulty operation of the lever 6h occurs. Thus, a situation in which a problem related to the faulty operation is left is removed, so the examination can be smoothly performed. In addition, the examination accuracy is improved.

For example, as shown in FIG. 15B, the operational detail information of the lever 6h is indicated to the person to be examined 4 in addition to the index, so the operational detail can be easily checked. Note that the operational detail information corresponding to the operation of the lever 6h can be also displayed separately from the index. For example, when the lever 6h is tilted to the right in the case of the Landolt ring 100 shown in FIG. 15A, the control portion 80 may control the liquid crystal display device 53 to set the Landolt ring 100 into an non-display state and display the arrow mark 102.

The operational detail information of the lever 6h may be outputted by voice. For example, when the lever 6h is tilted to the right in the case of the Landolt ring 100, corresponding announcement such as a voice message "the right is selected" may be outputted and give the operational detail information to the person to be examined 4. In this case, the voice message may be outputted while the operational detail information is displayed on the liquid crystal display device 53. Alternatively, only the voice message may be outputted.

When an index for requesting a specified direction to the person to be examined 4, which is represented by the Landolt ring 100 shown in FIG. 15A is used for the examination, information expressing the specified direction, such as the arrow mark 102 can be displayed to the person to be examined 4. A pattern of the information can be set as appropriate according to a kind of index to be used.

An index such as the RG chart 110 shown in FIG. 16, a chart composed of the pair of dot charts 120 and 121 shown in FIG. 17A, or the near chart 160 shown in FIG. 21A is used for the examination. The person to be examined compares among appearance states of the plurality of portions composing the index to select any one of the portions. In this case, information expressing the selected portion can be displayed to the person to be examined 4. At this time, the selected portion can be blinked as in the case of the RG chart 110. Alternatively, the frame surrounding the selected portion can be displayed as in the case of the dot charts 120 and 121 or the case of the near chart 160. When a display color of the selected portion is changed or only the selected portion is displayed, it is also possible to express the selected portion.

When astigmatic examination is performed using the fan chart 130 shown in FIG. 18A, the astigmatic axial angle corresponding to the rotational stop position of the mark M is automatically obtained, so the examination can be smoothly performed.

When an index for specifying a position on the index, such as the fan chart 130 shown in FIG. 18A or the cross chart shown in FIG. 20A is used for the examination, information expressing the specified position can be displayed to the person to be examined 4. With respect to a display pattern of the information, in addition to a pattern in which the specified position is surrounded by the frame, it is possible to suitably employ a pattern in which a color of the specified position is changed or a pattern in which only the specified position is displayed.

In the optometry apparatus 2, index indicating means for indicating the index to the person to be examined 4 and display means for displaying the operational detail information of the lever 6h to the person to be examined 4 compose the single liquid crystal display device 53 to simplify the apparatus. Note that, in the optometry apparatus according to the present invention, the index indicating means and the display means can be also composed of separate display devices such as liquid crystal display devices.

The optometry apparatus 2 is connected with the liquid crystal monitor 64q and the monitor device 91 serving as display means used for the operator. The operational detail information of the lever 6h operated by the person to be examined 4 can be also displayed on the display means for the operator by the control portion 80. Therefore, the operator can check the progress of the examination, the frequency of the faulty operation of the person to be examined 4, and the like, so exact advice can be provided to the person to be examined 4. Thus, the examination can be smoothly performed.

Second Embodiment

An optometry apparatus according to a second embodiment of the present invention will be described. The optometry apparatus according to this embodiment has substantially the same structure as that of the optometry apparatus 2 according to the first embodiment. A pattern of an index indicated to the person to be examined is different from that in the first embodiment. In the optometry apparatus according to this embodiment, an eyesight chart including a plurality of indices separately used for each examination is indicated. The eyesight chart is, for example, a conventional eyesight chart in which a plurality of Landolt rings are arranged for each eyesight value, an eyesight chart which rapidly becomes widespread in recent years and in which log MAR type indices (such as Landolt rings or alphabet indices) are arranged, or the like. Hereinafter, the optometry apparatus according to this embodiment (indicated by the same reference numeral 2) will be described based on an example of an eyesight chart using log MAR type Landolt rings as indices with reference to the structure of the optometry apparatus 2 according to the first embodiment.

Figure 22:
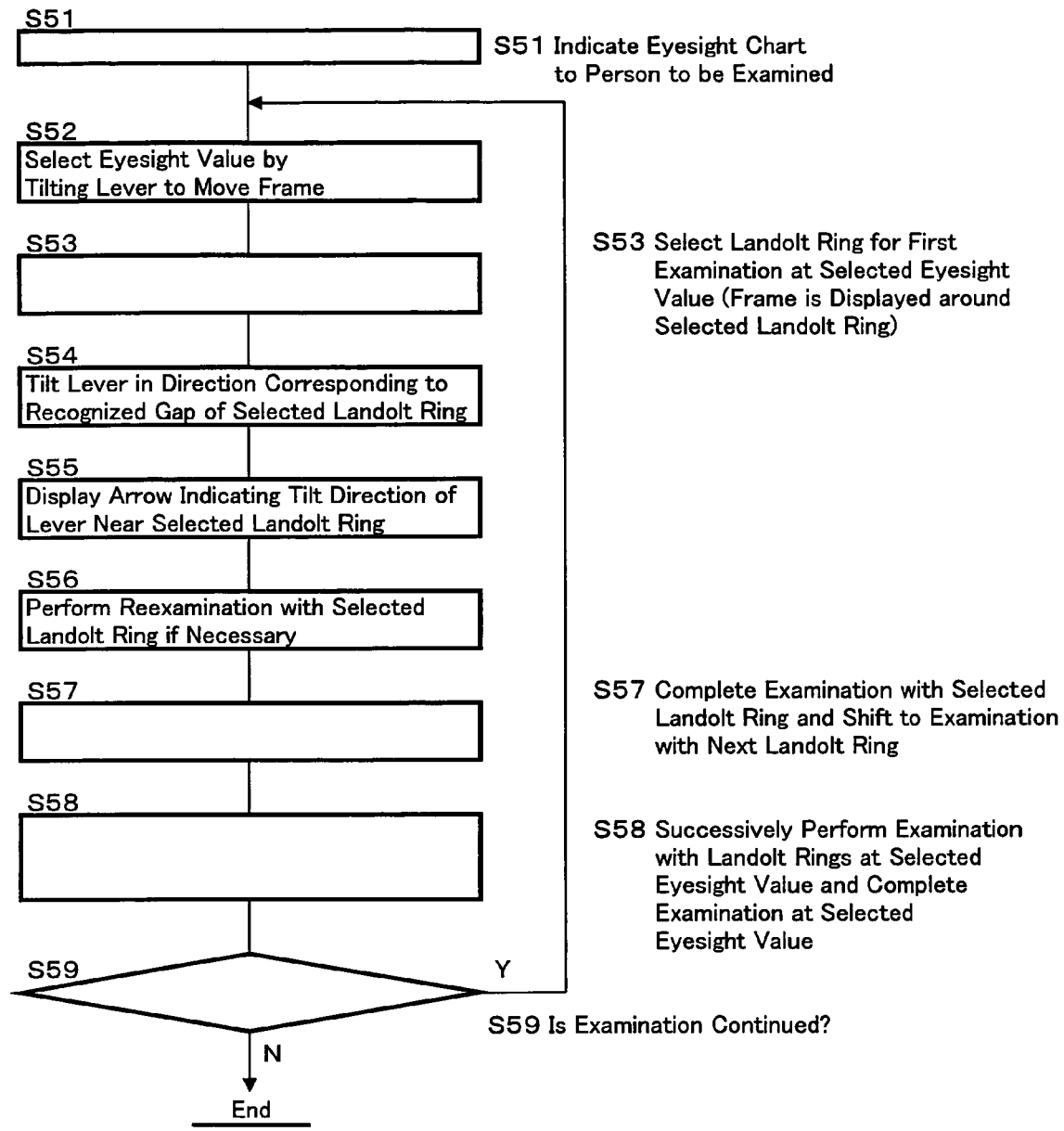
FIG. 22 is a flow chart showing an example of an examination procedure executed by an optometry apparatus according to a second embodiment of the present invention.
Figure 23:
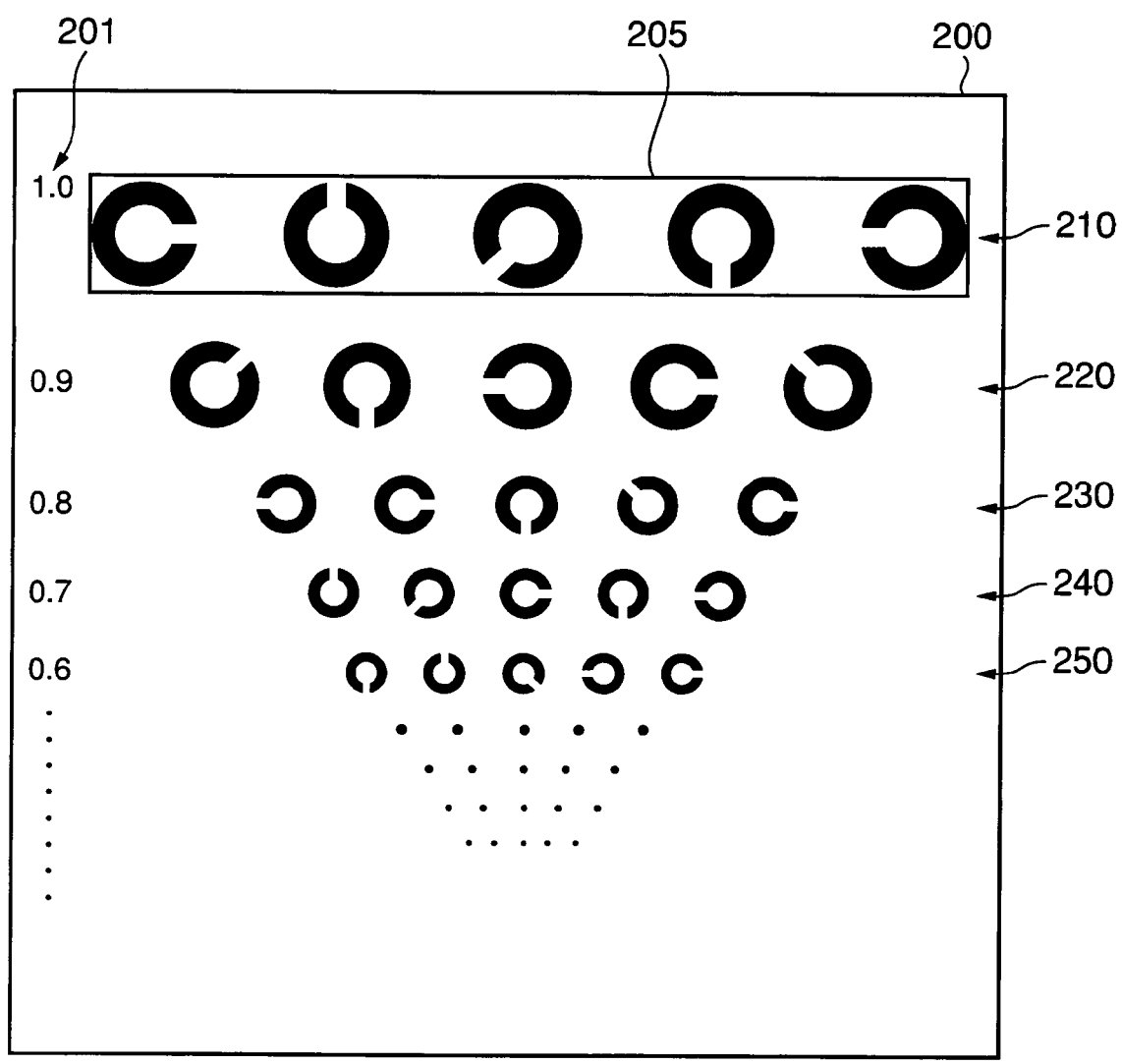
FIG. 23 is a schematic view showing an example of a display pattern of a log MAR type eyesight chart displayed to the person to be examined by the optometry apparatus according to the second embodiment of the present invention.

FIG. 22 is a flow chart showing an example of an examination procedure executed by the optometry apparatus 2 according to this embodiment. First, when the person to be examined 4 or the like performs predetermined examination start operation, a log MAR type eyesight chart 200 as shown in FIG. 23 is displayed on the liquid crystal display device 53 of each of the optical head portions 5*l* and 5*r* by the control portion 80 and is indicated to the person to be examined 4 (Step S51). The eyesight chart 200 includes an eyesight value display portion 201 in which log MAR type eyesight values of "1.0, 0.9, 0.8, . . ." are arranged in the vertical direction, index lines 210, 220, 230, . . . in which a plurality of Landolt rings corresponding to the eyesight values of 1.0, 0.9, 0.8, . . . , respectively, are arranged in the horizontal direction. A frame 205 surrounding the index line 210 corresponding to the eyesight value of 1.0 is displayed on the eyesight chart 200. Note that the frame 205 may be displayed around an index line other than the index line 210. The frame 205 composes the operational detail information in the present invention.

The person to be examined 4 tilts the joystick lever 6*h* in the lower direction to move the frame 205 downward to the index lines 220, 230, . . . according to, for example, a voice message outputted from the optometry apparatus 2, so a Landolt ring corresponding to an eyesight value which is an initial value for examination is selected (Step S52). When the frame 205 passes through a target eyesight value, the lever 6*h* is tilted upward to move the frame 205 upward, thereby selecting the target eyesight value. When the entire eyesight chart 200 cannot be displayed on the liquid crystal display device 53, the screen is scrolled up/down according to the upper and lower movements of the frame 205 corresponding to the upper and lower tilting of lever 6*h*. It is preferable to change a size of the frame 205 to be displayed according to a size of the Landolt ring for each eyesight value.

In the eyesight value selecting operation described in Step S52, for example, when the lever 6*h* is tilted downward (upward) one time, the eyesight value is reduced (increased) by one step. That is, when first lower tilting operation of the lever 6*h* is performed, the control portion 80 controls the liquid crystal display device 53 in response to an input signal from the lever 6*h* to set the frame 205 which is surrounding the index line 210 into an non-display state and display the frame 205 for surrounding the index line 220 corresponding to the eyesight value of 0.9. Subsequently, when second tilting operation is performed, similarly, the frame 205 which is surrounding the index line 220 is set into an non-display state and the frame 205 for surrounding the index line 230 corresponding to the eyesight value of 0.8 is displayed (same as above). Upper tilting operation of the lever 6*h* is similarly performed. Therefore, the frame 205 which is surrounding the index line 210 is moved to a position for surrounding the target index line 230. While the lever 6*h* is tilting, the eyesight value may be stepped up/down at predetermined intervals to select an eyesight value obtained when the lever 6*h* returns to a neutral position.

Figure 24:
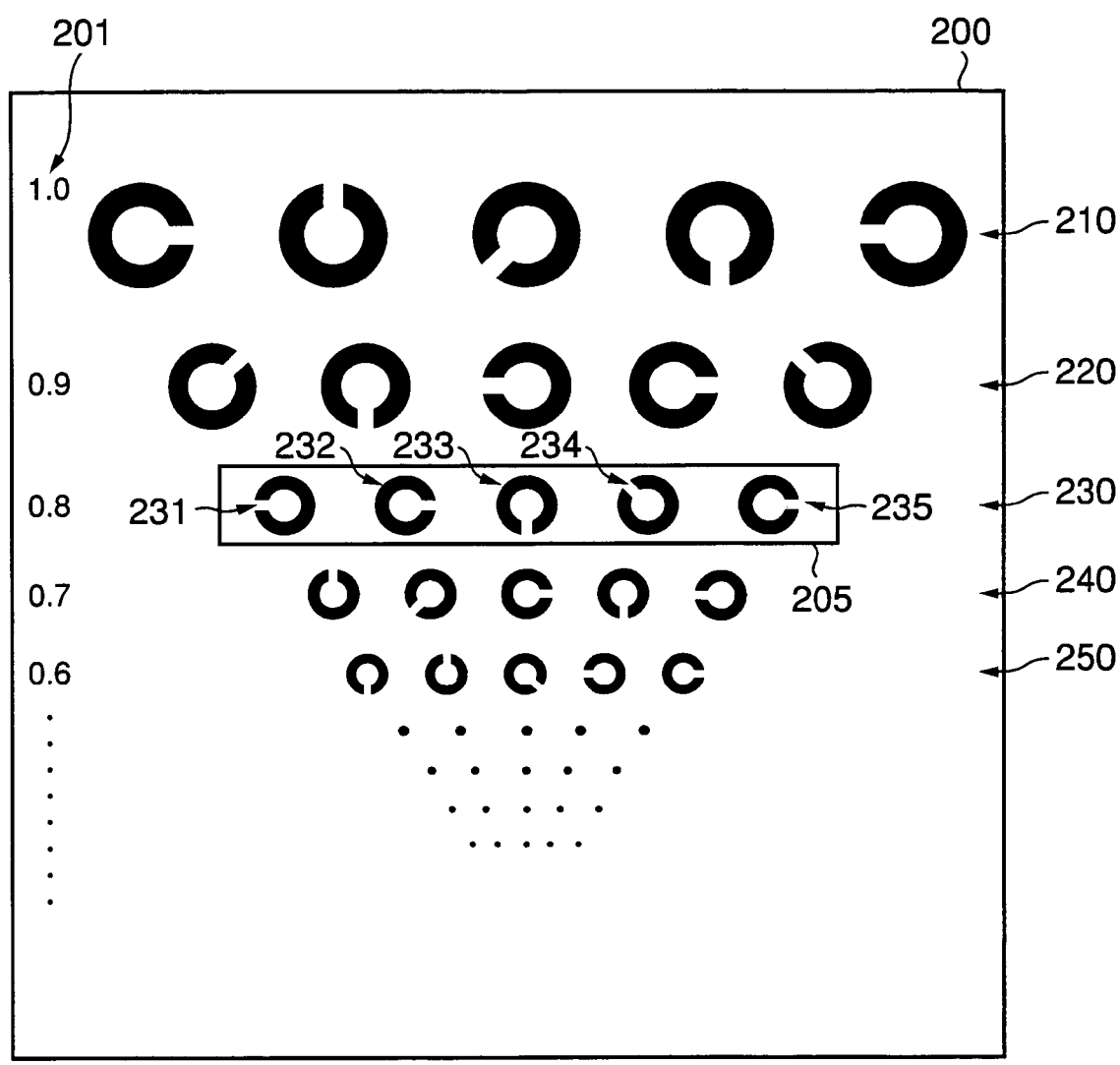
FIG. 24 shows a display pattern based on a reply of the person to be examined to the log MAR type eyesight chart displayed to the person to be examined by the optometry apparatus according to the second embodiment of the present invention.

FIG. 24 shows a display pattern of the eyesight chart 200 when the person to be examined 4 tilts the lever 6*h* downward two times to select the eyesight value of 0.8 in Step S52. Followed by a voice message or the like, the person to be examined 4 selects a Landolt ring used for first examination among Landolt rings 231 to 235 related to the eyesight value of 0.8 (Step S53). For example, when the lever 6*h* is tilted to the left, the leftmost Landolt ring 231 is selected and the frame 205 is displayed around the Landolt ring 231. On the other hand, when the lever 6*h* is tilted to the right, the rightmost Landolt ring 235 is selected and the frame 205 is displayed around the Landolt ring 235. The lever 6*h* may be tilted to the right or the left to select an arbitrary Landolt ring.

Figure 25:
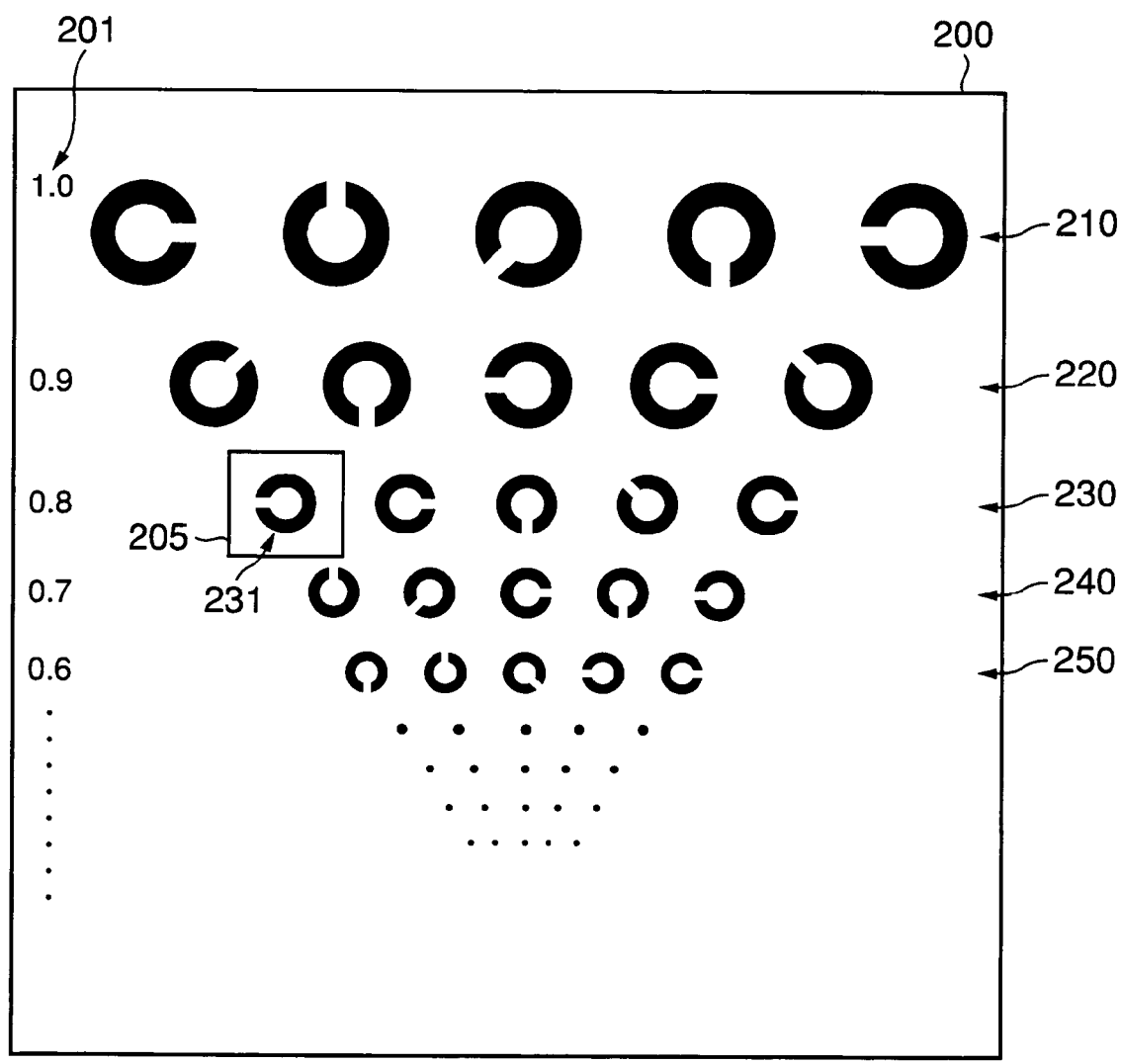
FIG. 25 shows a display pattern based on a reply of the person to be examined to the log MAR type eyesight chart displayed to the person to be examined by the optometry apparatus according to the second embodiment of the present invention.
Figure 26:
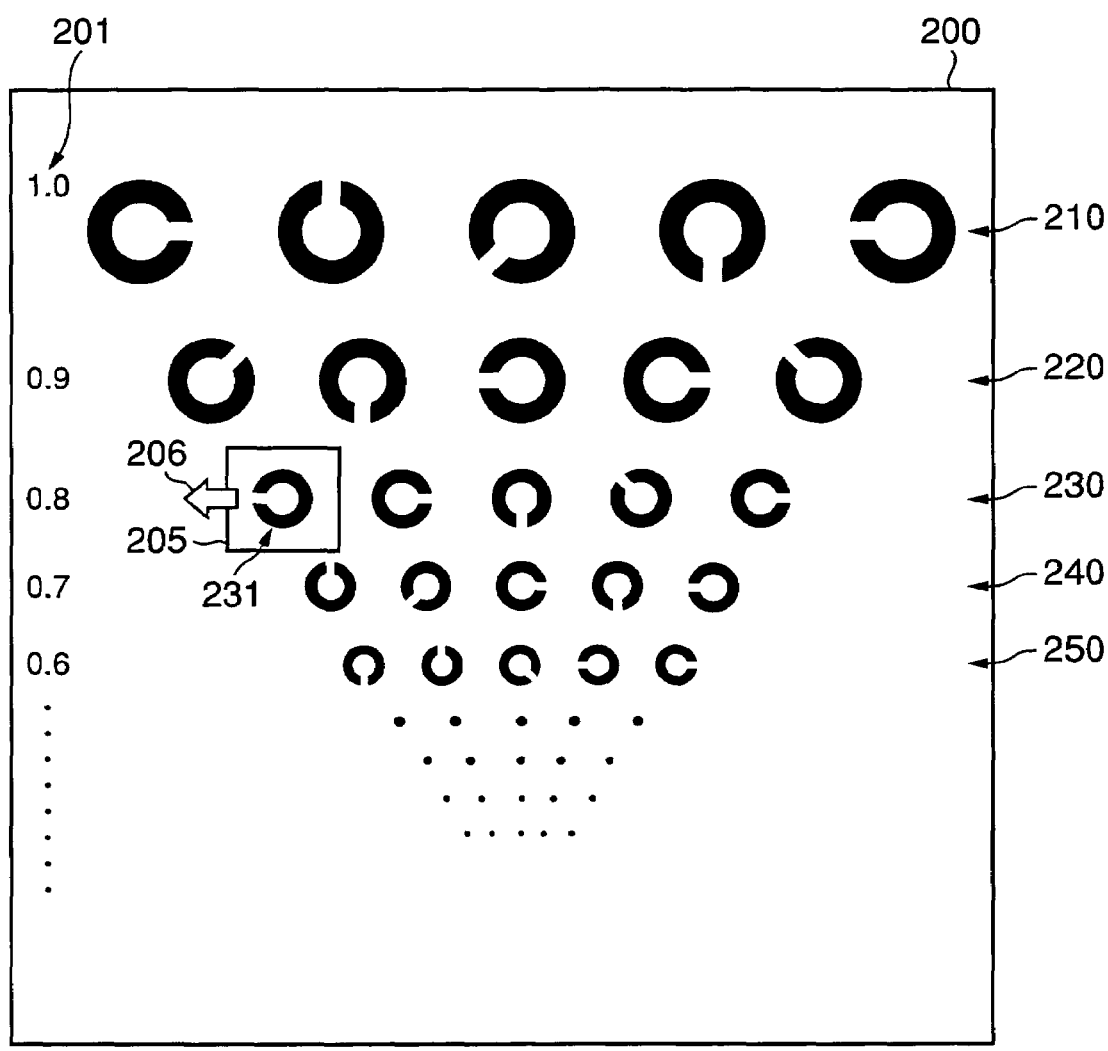
FIG. 26 shows a display pattern based on a reply of the person to be examined to the log MAR type eyesight chart displayed to the person to be examined by the optometry apparatus according to the second embodiment of the present invention.

FIG. 25 shows a display pattern of the eyesight chart 200 when the leftmost Landolt ring 231 is selected in Step S53. The person to be examined 4 views the Landolt ring 231 and tilts the lever 6*h* in the direction in which the person recognized that the gap exists (Step S54). The control portion 80 controls the liquid crystal display device 53 to display an arrow indicating the tilting direction of the lever 6*h* (operational detail information) near the Landolt ring 231 (Step S55). FIG. 26 shows a display pattern of the eyesight chart 200 when the lever 6*h* is tilted to the left. An arrow 206 corresponding to the tilting direction (left direction) of the lever 6*h* is displayed on the left side of the Landolt ring 231.

While the arrow is being displayed, the person to be examined 4 can perform reexamination using the Landolt ring 231 (Step S56). That is, when the lever 6*h* is operated while the arrow is being displayed (within a time measurement period from start to end), the control portion 80 sets the arrow into a non-display state and causes the liquid crystal display device 53 to display another arrow corresponding to a new tilting direction of the lever 6*h*. The reexamination can be performed up to, for example, three times in view of an examination time. For the reexamination processing, the control portion 80 starts to measure a predetermined time (for example, 5 seconds) using an internal timer simultaneously with the display of the arrow. After the completion of the time measurement, the arrow is set into the non-display state. The frame 205 is moved to the next Landolt ring 232. The optometry apparatus 2 shifts to the examination using the Landolt ring 232 (Step S57).

Therefore, examinations using the Landolt rings at the first eyesight value are successively performed and then the examinations at eyesight value are completed (Step S58). At this time, examinations using all the Landolt rings at the eyesight value may be performed or examinations using any of the Landolt rings may be performed. When the replies are successively correct or incorrect with respect to a predetermined number of Landolt rings (for example, three Landolt rings), the eyesight value for examination may be shifted to a next eyesight value. When the button 6*g* is pressed down before the examinations using all the Landolt rings at the eyesight value are completed, the examination at the eyesight value may be completed. In order to show the completion of the examination at the eyesight value, the frame 205 is displayed around all the Landolt rings at the eyesight value (that is, the display pattern returns to that shown in FIG. 23).

When the person to be examined 4 determines that further examination is necessary (Step S59; Y), the lever 6*h* is tilted upward or downward to move the frame 205 to a position corresponding to a next eyesight value, thereby performing the same examination (processing returns to Step S52). On the other hand, when the person to be examined 4 determines that further examination is unnecessary (Step S59; N), the examination using the eyesight chart 200 is completed.

Note that the determination as to whether the examination is continued or completed in Step S59 may be automatically performed by the control portion 80 based on, for example, the degree of correct reply in the examination. Similarly, next eyesight value selection in Step S60 may be automatically performed by the control portion 80.

According to the optometry apparatus 2 in this embodiment, the person to be examined 4 can recognize the operational detail of the lever 6*h* operated to select a desirable index from the plurality of indices displayed by a list based on the position of the frame 205. Therefore, whether or not faulty operation occurs can be easily checked. The index can be selected while the position of the frame 205 is checked, so it is possible to surely select a target index.

The same screen as that of the liquid crystal display device 53 can be displayed on the display means for the operator, such as the monitor device 91 by the control portion 80. Therefore, the operator can hold the progress of the examination of the person to be examined 4 and the degree of understanding on the examination.

The operational detail information for indicating the specified index to the person to be examined 4 is not limited to the frame 205. For example, it is possible to apply operational detail information which is color information for displaying the specified index using a color different from that of another index or operational detail information which is lightness information for brightly displaying only the specified index. In more general, it is sufficient to use operational detail information for clearly expressing the specified index by setting the index specified by the operation means such as the lever 6h into a display state different from that of another index.

Third Embodiment

Figure 27:
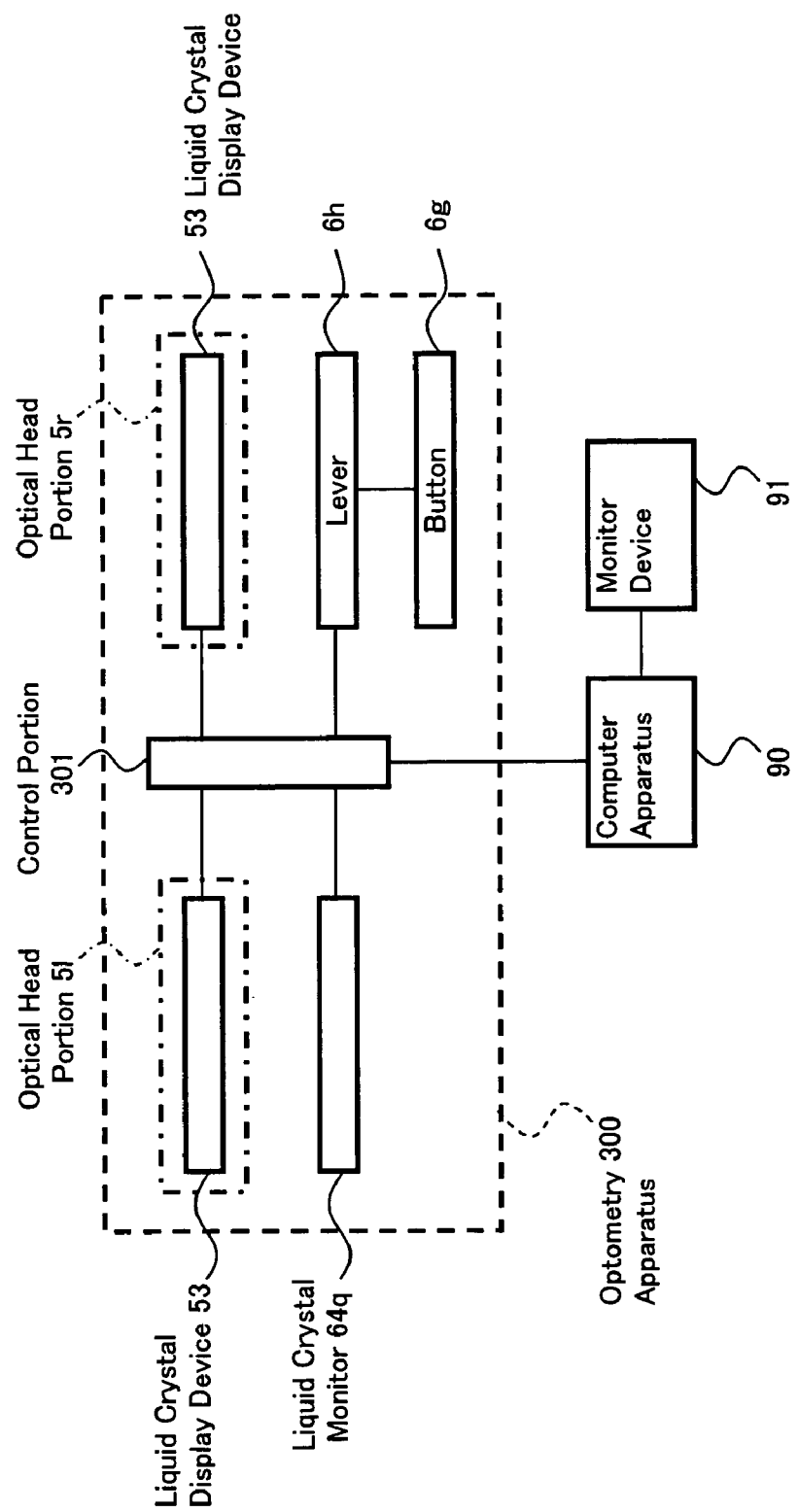
FIG. 27 is a schematic block diagram showing an example of a control system included in an optometry apparatus according to a third embodiment of the present invention.

An optometry apparatus according to a third embodiment of the present invention will be described. The optometry apparatus according to this embodiment has a structure for suitably dealing with faulty operation in the case where the person to be examined 4 performs the faulty operation. FIG. 27 is a block diagram showing an example of the optometry apparatus according to this embodiment. The optometry apparatus according to this embodiment has substantially the same structure as that of the optometry apparatus 2 according to the first embodiment. The same references are provided to the same portions as those in the first embodiment.

The optometry apparatus 300 shown in FIG. 27 includes the optical head portions 5l and 5r each having the liquid crystal display device 53, the joystick lever 6h, the button 6g located on the upper portion of the lever 6h, the liquid crystal monitor 64q, and a control portion 301 that executes processing described later. The control portion 301 is connected with the computer apparatus 90 for operator. The monitor device 91 is provided for the computer apparatus 90. The control portion 301 includes a storage device (such as a ROM) that stores control programs for controlling the respective portion of the apparatus and an arithmetic and control device (such as a CPU) that executes the control programs.

When the person to be examined 4 operates the lever 6h to input the reply to the indicated index, the control portion 301 controls the liquid crystal display device 53 based on an input signal related to the operation of the lever 6h to blink the operational detail information. At this time, it is preferable to display the operational detail information together with the index. Then, the control portion 301 measures a predetermined time period (for example, 5 seconds) using an internal timer. When the lever 6h is further operated within the predetermined time period, the control portion 301 controls the liquid crystal display device 53 to stop the display of the operational detail information which is being displayed and to display newly inputted operational detail information. The reentry processing can be performed many times during the predetermined time period. The measurement of the predetermined time may be performed again in response to the new operation of the lever 6h. After the measurement of the predetermined time period is completed, the control portion 301 switches the operational detail information blinked on the liquid crystal display device 53 to a normal display mode and causes the storage device or the like to store the operational detail information as determined information.

According to such a control mode, the person to be examined 4 can deal with faulty operation as follows. Hereinafter, the case where the reply to the Landolt ring 100 shown in FIG. 15A is inputted will be described. Assume that the person to be examined 4 tilts the lever 6h in the lower direction in the Landolt ring 100 with a right gap. Then, the control portion 301 controls the liquid crystal display device 53 to blink a downward arrow mark 102D located on the lower side of the Landolt ring 100 as shown in FIG. 28A. In addition, the control portion 301 causes the timer to start measurement of 5 seconds. Here, assume that the person to be examined 4 views the direction of the arrow mark 102D and finds faulty operation. Then, when the lever 6h is tilted to the right side before the measurement of 5 seconds is completed, the control portion 301 controls the liquid crystal display device 53 based on an input signal related to the operation of the lever 6h to display a rightward arrow mark 102R as shown in FIG. 28B as new operational detail information. Therefore, when the person to be examined 4 finds the faulty operation of the lever 6h, the reply can be speedily and easily inputted again. When the person to be examined 4 determines that the faulty operation does not occur and the measurement of 5 seconds is completed without reentry, the control portion 301 controls the liquid crystal display device 53 to switch the downward arrow mark 102D from a blinking display mode to the normal display mode. Similarly, in the cases of other indices, reentry can be performed. Note that the allowable number of reentry of the reply (for example, three times) may be set in advance, so a situation in which the examination is unnecessarily prolonged can be prevented from occurring.

The above-mentioned predetermined time period (reentry allowable time period) may be changeable according to an age and the like of the person to be examined 4, which are inputted at the time of the first examination. A relatively long reentry allowable time period (for example, 8 seconds) can be set to the person to be examined whose age is 60 or older. The reentry allowable time period may be changed according to the frequency of faulty operation of the person to be examined 4. When the faulty operation is performed predetermined times (for example, three times), the reentry allowable time period may be changed to a longer time. Therefore, whether or not the faulty operation occurs can be carefully determined.

(Modified Example)

A modified example of this embodiment will be described. An optometry apparatus 300' of this modified example (not shown) has the same structure as that shown in the block diagram of FIG. 7. In the optometry apparatus 300', when the button 6g is pressed down, reentry of the reply to the index is allowed.

When the reply to the index is inputted by the lever 6h, the control portion 301 causes the liquid crystal display device 53 to display operational detail information based on an input signal from the lever 6h. After that, when the button 6g is pressed down, the control portion 301 sets the operational detail information into a non-display state based on an input signal from the button 6g. That is, a display state is returned to a state in which only the index is indicated to the person to be examined 4. In addition, the control portion 301 controls the optometry apparatus 300' to becomes a state in which the reentry of the reply to the index is allowed. That is, the control portion 301 receives the reentry of the reply from the lever 6h as effective information and causes the liquid crystal display device 53 to display operational detail information of the reentry.

According to the optometry apparatus 300', when the person to be examined 4 finds the faulty operation after the input of the reply, the button 6g is pressed down to clear the input. Therefore, the reply can be inputted again. Thus, even when the person to be examined 4 performs faulty operation, the person to be examined 4 can suitably deal with the faulty operation.

As in the case of the optometry apparatus 300, when the reentry allowable time period is set in advance, reentry is allowed within the reentry allowable time period. In order that the person to be examined 4 recognize the reentry allowable time period, a message, a mark, or the like may be indicated or announcement may be outputted. The allowable number of reentry (for example, up to three times) can be also set.

According to the optometry apparatus 300 in this embodiment, when the person to be examined 4 finds the faulty operation, reentry can be speedily and easily performed.

In addition to the above-mentioned structures, it is sufficient that the optometry apparatus according to the present invention include reentry request operation means such as the button 6g or the lever 6h operated to input the reentry request to the faulty operation of the lever 6h and control means for allowing the reentry to the reply in response to the operation of the reentry request operation means and causing the liquid crystal display device 53 to display new operational detail information based on the reentry.

Fourth Embodiment

An optometry apparatus according to a fourth embodiment of the present invention will be described. The optometry apparatus according to this embodiment has a structure for suitably performing a trial operation of the lever 6h or the like during the examination. The trial operation is described in Step S3 of the flow chart shown in FIG. 13 and performed before an actual examination.

An optometry apparatus 400 according to this embodiment (not shown) has the same structure as that of the optometry apparatus 2 according to the first embodiment. Hereinafter, the optometry apparatus according to this embodiment will be described with reference to the block diagram shown in FIG. 12. In order to make the person to be examined 4 perform the trial operation of the lever 6h or the like, the control portion 80 causes the liquid crystal display device 53 to display a training screen for each process of the examination. The liquid crystal display device 53 composes "training screen display means" in the present invention. The person to be examined 4 performs the trial operation according to guide announcement or messages.

FIG. 29A shows a display pattern of a training screen indicated to the person to be examined 4 in order to perform the trial operation of the lever 6h or the like during eyesight measurement. A training screen 1000 shown in FIG. 29A includes the Landolt ring 100 identical to that shown in FIG. 15A and a guide message 1001. The message 1001 describes "TRIAL INPUT OF EYESIGHT EXAMINATION" which is the purpose of the screen and "PLEASE TILT THE LEVER IN A DIRECTION CORRESPONDING TO THE GAP" which is the operating method. In the training screen 1000, the arrow mark 102 is displayed corresponding to the direction of the gap 101 of the Landolt ring 100. When the person to be examined 4 views the arrow mark 102, the person can easily understand "A DIRECTION CORRESPONDING TO THE GAP" in the message 1001 is the direction of the arrow mark 102. Therefore, the person to be examined 4 can recognize that the lever 6h just needs to be tilted in the direction indicated by the arrow mark 102.

When the person to be examined 4 tilts the lever 6h, the control portion 80 determines whether or not the operating direction of the lever 6h is aligned with the direction indicated by the arrow mark 102 based on an input signal related to the operation of the lever 6h. When the operating direction of the lever 6h is determined to be aligned with the direction indicated by the arrow mark 102, the control portion 80 controls the liquid crystal display device 53 to set the message 1001 into a non-display state and to display a message "correct" 1002. In addition, the control portion 80 causes the liquid crystal display device 53 to blink the arrow mark 102, thereby emphasizing correct operation. The message 1002 and the blinking of the arrow mark 102 each are "correct information" in the present invention. Note that only one of the correct information may be displayed. The correct information may be outputted by voice.

Although not shown, when the operating direction of the lever 6h is not aligned with the direction indicated by the arrow mark 102, the control portion 80 causes the liquid crystal display device 53 to display a message such as "Lever operation is incorrect. Please input a reply again". Therefore, the input operation is requested again. The message is "incorrect information" in the present invention. The incorrect information may be outputted by voice.

The optometry apparatus 400 according to this embodiment can similarly display the training screen for the trial operation in the RG test, the cross cylinder test, the phoria examination, the near examination, the eyesight examination using the log MAR type indices, or the like.

According to the optometry apparatus 400, the trial input operation is performed with a state in which the person to be examined 4 looks in the optical head portions 5l and 5r, so it is unnecessary to use the monitor device 91 for operator as compared with a conventional case. Therefore, the person to be examined 4 can easily perform the trial input operation. According to the optometry apparatus 400, the trial operation automatically proceeds, the person to be examined 4 can easily perform the trial input operation alone. In addition, the trial operation can be performed with the same state as that in actual examination, so the improvement of understanding of the person to be examined 4 to the operating method can be expected.

Fifth Embodiment

An optometry apparatus according to a fifth embodiment of the present invention will be described. The optometry apparatus according to this embodiment relates to a structural example of the display means for displaying operational detail information corresponding to the operation of the lever 6h or the button 6g which is operated by the person to be examined 4. In the above-mentioned respective embodiments, the operational detail information is displayed on the liquid crystal display device 53. In addition, the liquid crystal display device 53 is used to indicate the index. The optometry apparatus according to this embodiment separately includes the index indicating means for indicating the index to the person to be examined 4 and the display means for displaying the operational detail information to the person to be examined 4.

Figure 30A:
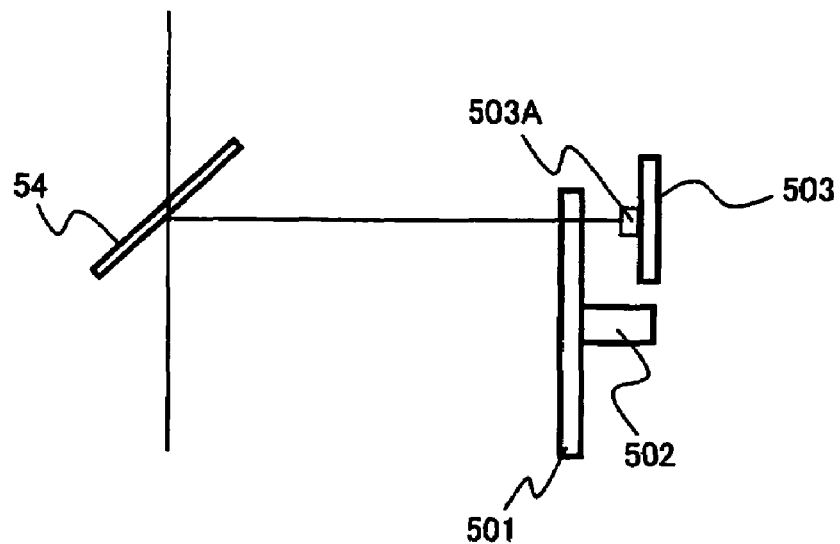
Figure 30B:
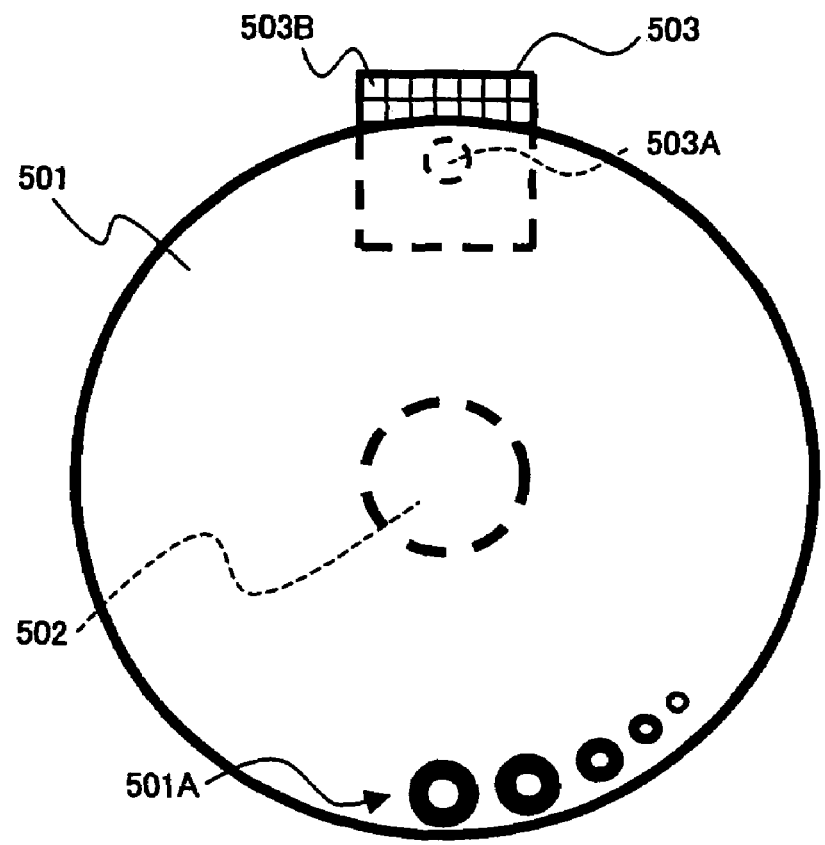
Figure 31:
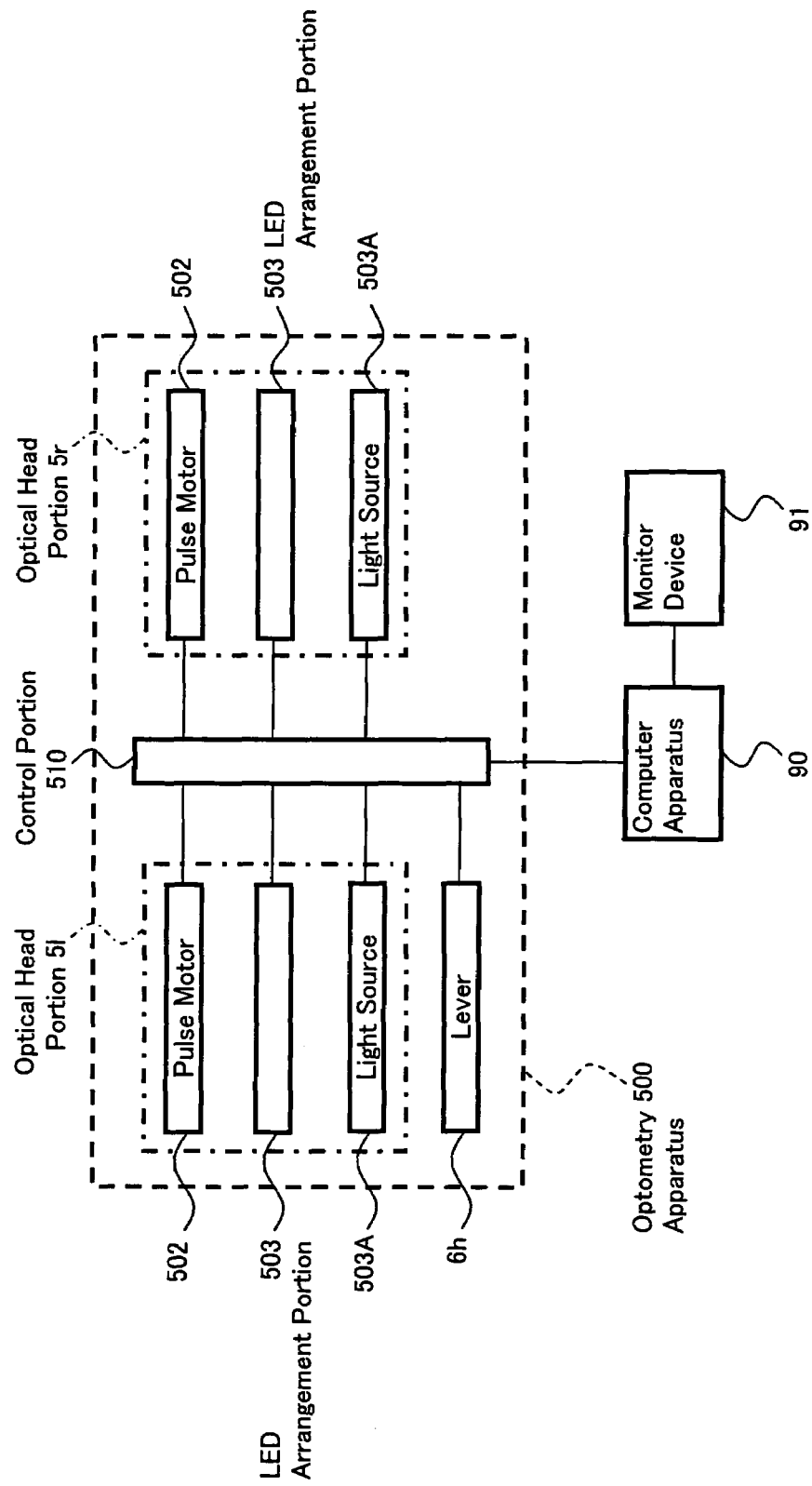
FIG. 31 is a schematic block diagram showing an example of a control system included in an optometry apparatus according to a fifth embodiment of the present invention.

FIGS. 30A and 30B show the index indicating means and the display means in an optometry apparatus 500 according to this embodiment. FIG. 30A is a side view showing the optometry apparatus and FIG. 30B a front view showing the optometry apparatus as viewed from the index indicating means side. Here, FIG. 30A shows the modification of a part of the optical system shown in FIG. 5. Reference numeral 54 denotes a half mirror shown in FIG. 5. FIG. 31 shows a control system of the optometry apparatus 500. The optometry apparatus 500 includes the optical head portions 5l and 5r, each of which has the structure as shown in FIGS. 30A and 30B.

As shown in FIGS. 30A and 30B, the optometry apparatus 500 includes an index plate 501 for indicating various indices to the person to be examined 4, a pulse motor 502 for rotating the index plate 501, and a LED arrangement portion 503 in which a plurality of LEDs (light emitting diodes; light emitting means) 503B are arranged on a surface located on the index plate 501 side. The LED arrangement portion 503 is provided such that the central position thereof is located on the optical axis of each of the fixation optical systems 32L and 32R. The LED arrangement portion 503 has a light source 503A provided in a central portion thereof.

Various indices 501A are arranged near the circumference of the index plate 501. In FIG. 30B, only the Landolt rings are shown. In actual, the RG chart, the dot charts, the fan chart, the cross chart, the near chart, the log MAR type eyesight chart, and the like are drawn on the index plate 501. The index plate 501 is made of a transparent material such as plastic or reinforced glass. When the light source 503A is turned on, the index 501A located on the optical axis of each of the fixation optical systems 32L and 32R is projected to each of the eyes to be examined EL and ER.

As shown in FIG. 31, the optometry apparatus 500 is composed of a control portion 510 serving as a main component. The control portion 510 includes a storage device (such as a ROM) that stores control programs and an arithmetic and control device (such as a CPU) that executes the control programs. The control portion 510 controls the pulse motor 502, the LED arrangement portion 503, and the light source 503A in each of the optical head portions 5*l* and 5*r*. More specifically, the control portion 510 controls the pulse motor 502 to rotate the index plate 501. Therefore, the target index 501A is located on the optical axis (of each of the fixation optical systems 32L and 32R). The control portion 510 controls turning on/off of each LED 503B on the LED arrangement portion 503. The control portion 510 also controls turning on/off of the light source 503A. The optometry apparatus 500 having such a structure executes the following operation.

When eyesight examination is performed on the eyes to be examined EL and ER, the control portion 510 controls the pulse motor 502 to rotate the index plate 501, so the Landolt ring is located on the optical axis. Then, the light source 503A is turned on. Therefore, the Landolt ring is indicted to each of the eyes to be examined EL and ER. In reply to this, when the person to be examined operates the lever 6*h*, the control portion 510 controls the LED arrangement portion 503 based on an input signal related to the operation of the lever 6*h* to display the operational detail information in the direction corresponding to the tilting of the level 6*h*. For example, the plurality of LEDs 503B are turned on to form the arrow mark 102 as shown in FIG. 15B.

In the case of the cross cylinder test, the control portion 510 controls to rotate the index plate 501, so the dot charts are located on the optical axis. Then, the light source 503A is turned on. Therefore, the dot charts are indicated to each of the eyes to be examined EL and ER. In reply to this, when the person to be examined operates the lever 6*h*, the control portion 510 controls the LED arrangement portion 503 based on an input signal related to the operation of the lever 6*h* to display the operational detail information corresponding to the operation of the lever 6*h*. For example, the plurality of LEDs 503B are turned on to form a frame 123 as shown in FIG. 17B.

Even in other examinations, the LEDs 503B are suitably turned on or blinked, so the same operation as that of the optometry apparatus 2 according to the first embodiment can be realized. Therefore, the person to be examined 4 can check whether or not the faulty operation occurs.

Instead of the index plate 501, a transmission liquid crystal display device, that is, a liquid crystal display device constructed to transmit a light flux from a background light source (for example, the light source 503A) may be used to indicate the index to the person to be examined. Instead of the LED arrangement portion 503, a liquid crystal display device or the like may be used. A member other than the LED may be used for light emitting means in the present invention. For example, a lamp is provided in the rear of a light shielding plate having a light transmission portion with an arrow shape. Therefore, the arrow mark 102 can be formed by turning on of the lamp.

[Another Application Example]

Another application example of the optometry apparatus according to the present invention will be described. This example relates to an optometry apparatus including an eyesight chart (apparatus) as the index indicating means used to simultaneously indicate different indices to the right and left eyes to be examined based on a polarizing characteristic. The index indicated using the eyesight chart is called a polarizing index or the like (for example, see JP 07-043651 A).

The eyesight chart includes a plurality of arbitrary indices such as the Landolt rings, the fan chart, and an index for binocular visual performance examination, which are provided thereon. A polarizing film having polarizing axes in directions orthogonal to each other is bonded to an index indicating surface (surface facing the person to be examined) of the eyesight chart. When the person to be examined puts on spectacles including a pair of left and right polarizing lenses each having polarizing axes in two directions (which is called polarizing spectacles or the like), different indices are indicated to the right and left eyes to be examined. For example, assume that the indices simultaneously indicated to the right and left eyes to be examined are a first index and a second index, a polarizing characteristic provided to the first index is in a vertical direction, and a polarizing characteristic provided to the second index is in a horizontal direction. In addition, assume that a polarizing characteristic provided to the left eye to be examined is in a vertical direction and a polarizing characteristic provided to the right eye to be examined is in a horizontal direction. Here, in view of setting of polarizing characteristics, the first index is indicated to the left eye to be examined and the second index is indicated to the right eye to be examined. Note that the polarizing spectacles compose the polarization means in the present invention. In addition to the polarizing spectacles, an arbitrary polarizing element for providing a polarizing characteristic in the same direction as that of the first index to the left eye to be examined and providing a polarizing characteristic in the same direction as that of the second index to the right eye to be examined, such as a polarizing plate &an be used as the polarization means.

The optometry apparatus of this example includes the operation means for specifying an index shown on an eyesight chart and making a reply to the index, such as an operating lever, a track ball, or an operating panel. The person to be examined performs the operation in the same procedure as that in the case of the second embodiment. For example, when the person to be examined selects an index, only the selected index on the eyesight chart is lighted or a frame is displayed around the index. That is, the selected index is displayed in a display state different from that of another index. When a reply to the index is inputted, an operational detail of the operation means is displayed as operational detail information on the eyesight chart. Therefore, in this example, the eyesight chart composes the display means in the present invention. The above-mentioned display control is executed by the computer apparatus connected with both the operation means and the eyesight chart (apparatus) or the arithmetic and control device such as a CPU, which is provided in the eyesight chart (apparatus).

The above-mentioned detailed structures are merely examples of the optometry apparatus according to the embodiments of the present invention. Thus, various modifications can be made without departing from the gist of the present invention.

What is claimed is:

1. An optometry apparatus, comprising:
   index indicating means for indicating an index to each of right and left eyes of a person to be examined;
   operation means for inputting a reply to the index, which is operated by the person to be examined, the reply to the index being performed by specifying a direction by the operation means;
   display means for displaying the index and operational detail information expressing the direction specified by the operation means to the person to be examined;
   reentry request operation means for requesting reentry of the reply to the index for the predetermined time, which is operated by the person to be examined; and
   control means for setting the displayed operational detail information into a non-display state and enabling the reentry of the reply to the index when the reentry request operation means is operated.

2. An optometry apparatus according to the claim 1, wherein:
   the index indicating means comprises an eyesight chart including a first index to which a polarizing characteristic in a predetermined direction is provided and a second index to which a polarizing characteristic in a direction perpendicular to the predetermined direction is provided; and
   the optometry apparatus further comprises polarization means for providing the polarizing characteristic in the predetermined direction to the left eye to be examined to make visual recognition of the first index and providing the polarizing characteristic in the direction perpendicular to the predetermined direction to the right eye to be examined to make visual recognition of the second index.

3. An optometry apparatus according to the claim 1, wherein:
   the display means blinks the operational detail information for a predetermined time;
   the reentry request operation means is operated for requesting reentry of the reply to the index for the predetermined time; and
   the control means is configured to set the blinked operational detail information into a non-display state and to enable the reentry of the reply to the index when the reentry request operation means is operated.

4. An optometry apparatus according to the claim 3, wherein the index indicating means and the display means are each composed of a single liquid crystal display device.

5. An optometry apparatus according to the claim 3, wherein:
   the display means comprises a plurality of light emitting devices arranged around the index indicated by the index indicating means; and
   the display means displays the operational detail information by turning on a light emitting device located at a position corresponding to operation of the operation means.

6. An optometry apparatus according to the claim 1, further comprising training screen displaying means for displaying a training screen for training an operating method of the operation means for various examinations to the person to be examined, wherein:
   when input operation executed by the operation means on the training screen is fit to the operating method, the display means displays correct information indicating that the input operation is correct as the operational detail information; and
   when the input operation is not fit to the operating method, the display means displays incorrect information indicating that the input operation is incorrect as the operational detail information.

7. An optometry apparatus according to the claim 1, wherein the index indicating means and the display means are each composed of a single liquid crystal display device.

8. An optometry apparatus according to the claim 1, wherein:
   the display means comprises a plurality of light emitting devices arranged around the index indicated by the index indicating means; and
   the display means displays the operational detail information by turning on a light emitting device located at a position corresponding to operation of the operation means.

9. An optometry apparatus, comprising:
   index indicating means for indicating an index to each of right and left eyes of a person to be examined;
   operation means for inputting a reply to the index, which is operated by the person to be examined, the index being composed of a plurality of parts, the reply to the index being performed by selecting any one of the plurality of parts by the operation means;
   display means for displaying the index and operational detail information expressing the part of the index selected by the operation means to the person to be examined;
   reentry request operation means for requesting reentry of the reply to the index for the predetermined time, which is operated by the person to be examined; and
   control means for setting the displayed operational detail information into a non-display state and enabling the reentry of the reply to the index when the reentry request operation means is operated.

10. An optometry apparatus according to the claim 9, wherein:
    the index indicating means comprises an eyesight chart including a first index to which a polarizing characteristic in a predetermined direction is provided and a second index to which a polarizing characteristic in a direction perpendicular to the predetermined direction is provided; and
    the optometry apparatus further comprises polarization means for providing the polarizing characteristic in the predetermined direction to the left eye to be examined to make visual recognition of the first index and providing the polarizing characteristic in the direction perpendicular to the predetermined direction to the right eye to be examined to make visual recognition of the second index.

11. An optometry apparatus according to the claim 10, wherein:
    the display means blinks the operational detail information for a predetermined time;

the reentry request operation means is operated for requesting reentry of the reply to the index for the predetermined time; and the control means is configured to set the blinked operational detail information into a non-display state and to enable the reentry of the reply to the index when the reentry request operation means is operated.

12. An optometry apparatus according to the claim 10, further comprising training screen displaying means for displaying a training screen for training an operating method of the operation means for various examinations to the person to be examined, wherein:

when input operation executed by the operation means on the training screen is fit to the operating method, the display means displays correct information indicating that the input operation is correct as the operational detail information; and when the input operation is not fit to the operating method, the display means displays incorrect information indicating that the input operation is incorrect as the operational detail information.

13. An optometry apparatus according to the claim 10, wherein the index indicating means and the display means are each composed of a single liquid crystal display device.

14. An optometry apparatus according to the claim 10, wherein:

the display means comprises a plurality of light emitting devices arranged around the index indicated by the index indicating means; and the display means displays the operational detail information by turning on a light emitting device located at a position corresponding to operation of the operation means.

15. An optometry apparatus according to the claim 9, wherein:

the display means blinks the operational detail information for a predetermined time;

the reentry request operation means is operated for requesting reentry of the reply to the index for the predetermined time; and the control means is configured to set the blinked operational detail information into a non-display state and to enable the reentry of the reply to the index when the reentry request operation means is operated.

16. An optometry apparatus according to the claim 9, further comprising training screen displaying means for displaying a training screen for training an operating method of the operation means for various examinations to the person to be examined, wherein:

when input operation executed by the operation means on the training screen is fit to the operating method, the display means displays correct information indicating that the input operation is correct as the operational detail information; and when the input operation is not fit to the operating method, the display means displays incorrect information indicating that the input operation is incorrect as the operational detail information.

17. An optometry apparatus according to the claim 9, wherein the index indicating means and the display means are each composed of a single liquid crystal display device.

18. An optometry apparatus according to the claim 9, wherein:

the display means comprises a plurality of light emitting devices arranged around the index indicated by the index indicating means; and the display means displays the operational detail information by turning on a light emitting device located at a position corresponding to operation of the operation means.

19. An optometry apparatus, comprising:

index indicating means for indicating an index to each of right and left eyes of a person to be examined;

operation means for inputting a reply to the index, which is operated by the person to be examined, the reply to the index being performed by specifying a position on the index by the operation means;

display means for displaying the index and operational detail information expressing the position specified by the operation means to the person to be examined;

reentry request operation means for requesting reentry of the reply to the index for the predetermined time, which is operated by the person to be examined; and control means for setting the displayed operational detail information into a non-display state and enabling the reentry of the reply to the index when the reentry request operation means is operated.

20. An optometry apparatus according to claim 19, wherein:

the index comprises a fan chart used for astigmatic examination;

the display means displays a mark rotating about a central position of the fan chart to the person to be examined; and the reply is performed by operating the operation means to stop the mark which is rotating at a position corresponding to a visually dense portion on the fan chart.

21. An optometry apparatus according to claim 20, further comprising means for obtaining an astigmatic axial angle corresponding to the position on the fan chart when the mark stops rotating.

22. An optometry apparatus according to claim 19, wherein:

the index comprises a cross chart used for phoria examination; and the optometry apparatus further comprises calculation means for calculating prism power corresponding to a predetermined position of the cross chart when the predetermined position is specified by the operation means.

23. An optometry apparatus according to the claim 19, wherein:

the index indicating means comprises an eyesight chart including a first index to which a polarizing characteristic in a predetermined direction is provided and a second index to which a polarizing characteristic in a direction perpendicular to the predetermined direction is provided; and the optometry apparatus further comprises polarization means for providing the polarizing characteristic in the predetermined direction to the left eye to be examined to make visual recognition of the first index and providing the polarizing characteristic in the direction perpendicular to the predetermined direction to the right eye to be examined to make visual recognition of the second index.

24. An optometry apparatus according to the claim 19, wherein:

the display means blinks the operational detail information for a predetermined time;

the reentry request operation means is operated for requesting reentry of the reply to the index for the predetermined time; and the control means is configured to set the blinked operational detail information into a non-display state and to enable the reentry of the reply to the index when the reentry request operation means is operated.

25. An optometry apparatus according to the claims 19, further comprising training screen displaying means for displaying a training screen for training an operating method of the operation means for various examinations to the person to be examined, wherein:

when input operation executed by the operation means on the training screen is fit to the operating method, the display means displays correct information indicating that the input operation is correct as the operational detail information; and when the input operation is not fit to the operating method, the display means displays incorrect information indicating that the input operation is incorrect as the operational detail information.

26. An optometry apparatus according to the claim 19, wherein the index indicating means and the display means are each composed of a single liquid crystal display device.

27. An optometry apparatus according to the claim 19, wherein:

the display means comprises a plurality of light emitting devices arranged around the index indicated by the index indicating means; and the display means displays the operational detail information by turning on a light emitting device located at a position corresponding to operation of the operation means.

28. An optometry apparatus, comprising:

index indicating means for indicating an eyesight chart including a plurality of indices to each of right and left eyes of a person to be examined;

operation means for inputting a reply to an index included in the indicated eyesight chart, which is operated by the person to be examined, the operating means being operated to select and specify the index included in the indicated eyesight chart;

display means for displaying the indicated index and operational detail information expressing the index specified by the operation means to the person to be examined;

reentry request operation means for requesting reentry of the reply to the index for the predetermined time, which is operated by the person to be examined; and control means for setting the displayed operational detail information into a non-display state and enabling the reentry of the reply to the index when the reentry request operation means is operated.

* * * * *